(12) United States Patent
Auzely-Velty et al.

(10) Patent No.: US 11,807,726 B2
(45) Date of Patent: Nov. 7, 2023

(54) METHOD OF CROSSLINKING GLYCOSAMINOGLYCANS

(71) Applicants: Galderma Research & Development, Biot (FR); Centre National de la Recherche Scientifique, Paris (FR)

(72) Inventors: Rachel Auzely-Velty, Grenoble (FR); Tamiris Figueiredo, Saint Martin d'Heres (FR); Laura Jing Jing, Antibes (FR); Craig Steven Harris, Biot (FR); Jean-Guy Boiteau, Opio (FR); Thibaut Gerfaud, Mouans Satoux (FR); Loic Tomas, Le Biot (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 17/535,314

(22) Filed: Nov. 24, 2021

(65) Prior Publication Data
US 2022/0081519 A1 Mar. 17, 2022

Related U.S. Application Data

(63) Continuation of application No. 16/322,615, filed as application No. PCT/EP2017/069574 on Aug. 2, 2017, now Pat. No. 11,214,655.

(60) Provisional application No. 62/370,479, filed on Aug. 3, 2016.

(30) Foreign Application Priority Data

Dec. 23, 2016 (EP) .................................... 16206624

(51) Int. Cl.
| | | |
|---|---|---|
| C08J 3/075 | (2006.01) |
| C08L 5/08 | (2006.01) |
| C08K 5/55 | (2006.01) |
| C08K 5/1545 | (2006.01) |
| C08J 3/24 | (2006.01) |
| C08B 37/00 | (2006.01) |
| C08B 37/08 | (2006.01) |
| A61K 31/728 | (2006.01) |

(52) U.S. Cl.
CPC .............. *C08J 3/075* (2013.01); *A61K 31/728* (2013.01); *C08B 37/0063* (2013.01); *C08B 37/0072* (2013.01); *C08J 3/24* (2013.01); *C08K 5/1545* (2013.01); *C08K 5/55* (2013.01); *C08L 5/08* (2013.01); *C08J 2305/08* (2013.01); *C08L 2203/02* (2013.01); *C08L 2312/00* (2013.01)

(58) Field of Classification Search
CPC .............. C08B 37/0063; C08B 37/0072; C08L 2312/00; C08L 5/08
See application file for complete search history.

(56) References Cited

U.S. PATENT DOCUMENTS

| | | | |
|---|---|---|---|
| 9,549,987 B2 * | 1/2017 | Auzely-Velty | C08B 37/0072 |
| 2013/0129797 A1 | 5/2013 | Gupta et al. | |
| 2014/0155305 A1 | 6/2014 | Hartshorne et al. | |
| 2016/0123988 A1 | 5/2016 | Lin et al. | |

FOREIGN PATENT DOCUMENTS

| | | |
|---|---|---|
| CN | 102772823 A | 11/2012 |
| CN | 105646732 A | 6/2016 |
| JP | 2015-208369 A | 11/2015 |
| WO | WO-97/04012 A1 | 2/1997 |
| WO | WO-98/02204 A1 | 1/1998 |
| WO | WO-2007/124132 A2 | 11/2007 |
| WO | WO-2014/072330 A1 | 5/2014 |

OTHER PUBLICATIONS

Tarus (Macromolecular Rapid Communications, 2014, 35, 2089-2095).*
Hall D.G., "Structure, Properties, and Preparation of Boronic Acid Derivatives", Overview of Their Reactions and Applications, 2011, Boronic Acids: Preparation and Applications in Organic Synthesis, Medicine and Materials, Second Edition, Wiley-VCH Verlag GmbH & Co. (134 pages).
International Search Report for PCT/EP2017/069574 dated Sep. 4, 2017.
Kotsuchibashi et al., "Temperature, pH, and Glucose Responsive Gels via Simple Mixing of Boroxole-and Glyco-Based Polymers", ACS Macro Letters; 2013 (2); pp. 260-264 (5 pages).
Lauder et al., "Chondroitin sulphate: A complex molecule with potential impacts on a wide range of biological systems" Elsevier, Complementary Therapies in Medicine, 2009, vol. 17, pp. 56-62.
Written Opinion for PCT/EP2017/069574 dated Sep. 4, 2017.
Gao et al (2010) "Mixture of Sodium Hyaluronate,Glycerin and Fructose Used for Submucosal Injection in Endoscopic Submucosal Dissection:Clinical Analysis of 26 Cases" Chin J Gastroenterol 15(5), pp. 299-301 with English Abstract.
International Search Report for PCT/EP2017/069576 dated Sep. 11, 2017.
Li J et al (2003) 11 Culture of hepatocytes on fructose-modified chitosan scaffolds 11, Biomaterials, Elsevier, Amsterdam, NL, vol. 24, No. 13, Jun. 1, 2003, pp. 2317-2322.
Search Report issued in European application No. 20172239 dated Sep. 25, 2020.
Written Opinion for PCT/EP2017/069576 dated Sep. 11, 2017.

* cited by examiner

*Primary Examiner* — Pancham Bakshi
(74) *Attorney, Agent, or Firm* — Sunit Talapatra; Foley & Lardner LLP

(57) ABSTRACT

A new hydrogel made of crosslinked glycosaminoglycans, particularly crosslinked hyaluronic acid, chondroitin or chondroitin sulfate, having reversible linkages using boronic acid or boroxole derivatives leading to new benefits. Glycosaminoglycans that are crosslinked via an alkoxyboronate ester anion formed between a diol portion of a diol-functional moiety grafted to a first glycosaminoglycan and a boronate hemiester grafted to a second glycosaminoglycan.

4 Claims, 9 Drawing Sheets

METHOD OF CROSSLINKING GLYCOSAMINOGLYCANS

CROSS-REFERENCE TO RELATED APPLICATION

This application is a continuation application of U.S. Ser. No. 16/322,615 filed Feb. 1, 2019, which application is a U.S. National Stage of PCT/EP2017/069574, filed Aug. 2, 2017, which application claims priority under 35 U.S.C. § 119 of U.S. Provisional Application No. 62/370,479, filed Aug. 3, 2016; and European Patent Application No. 16206624.5, filed Dec. 23, 2016, each hereby expressly incorporated by reference in its entirety and each assigned to the assignee hereof.

TECHNICAL FIELD OF THE INVENTION

The present invention relates to the field of hydrogels containing crosslinked polysaccharides and the use of such hydrogels in medical and/or cosmetic applications. More specifically, the present invention is concerned with hydrogels made of crosslinked glycosaminoglycans, particularly crosslinked hyaluronic acid, chondroitin or chondroitin sulfate, having reversible linkages, preferably boronate ester bonds, leading to new benefits.

BACKGROUND OF THE INVENTION

Water-absorbing gels, or hydrogels, are widely used in the biomedical field. They are generally prepared by chemical crosslinking of polymers to infinite networks. While many polysaccharides absorb water until they are completely dissolved, crosslinked gels of the same polysaccharides can typically absorb a certain amount of water until they are saturated, i.e. they have a finite liquid retention capacity, or swelling degree.

Hyaluronic acid, chondroitin and chondroitin sulfate are well-known biocompatible polymers. They are naturally occurring polysaccharides belonging to the group of glycosaminoglycans (GAGs). All glycosaminoglycans are negatively charged heteropolysaccharide chains which have a capacity to absorb large amounts of water.

Chondroitin sulfate (CS) is a highly abundant glycosaminoglycan found in the connective tissues of mammals where it, together with other sulfated glycosaminoglycans, is bound to proteins as part proteoglycans. It has previously been shown that hydrogels containing CS successfully can be used in biomedical applications due to their resemblance to the natural extra cellular matrix (Lauder, R. M., Complement Ther Med 17: 56-62, 2009). Chondroitin sulfate is also used in the treatment of osteoarthritis, e.g. as a dietary supplement.

Crosslinking of the glycosaminoglycans prolongs the duration of the degradable polymers that make up the network, which is useful in many applications.

However, one of the main drawbacks of a large majority of the glycosaminoglycans-based gels, such as when used for treating wrinkles lies in the difficulty of injecting the hydrogel due to the high crosslinking density of the polysaccharide.

Hyaluronic acid is one of the most widely used biocompatible polymers for medical use. Hyaluronic acid and the other glycosaminoglycans are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

Since hyaluronic acid is present with identical chemical structure except for its molecular mass in most living organisms, it gives a minimum of foreign body reactions and allows for advanced medical uses. Crosslinking and/or other modifications of the hyaluronic acid molecule is typically necessary to improve its duration in vivo. Furthermore, such modifications affect the liquid retention capacity of the hyaluronic acid molecule. As a consequence thereof, hyaluronic acid has been the subject of many modification attempts.

In the prior art, the hydrogels are prepared by reacting hyaluronic acid, for example, with BDDE (butanediol diglycidyl ether) in a basic aqueous medium resulting in the formation of covalent linkages (WO 97/04012). This is not a reversible process. WO 2014/072330 discloses a polymer composition comprising a mixture of phenylboronic acid modified hyaluronic acid polymer grafted on at least a hydroxyl with a group comprising phenylboronic acid and a cis-diol modified HA polymer grafted on at least a hydroxyl with a group comprising a cis-diol. US 2014/0155305 discloses an aqueous solution comprising a thickening polymer with diol groups distributed along it, such as guar or other polysaccharide, which is cross linked with a cross-linker which contains a plurality of boroxole groups. US 2013/0129797 A1 discloses polymeric compositions that comprise at least one polymer residue and at least one crosslinking moiety, wherein the polymer residue is crosslinked by the crosslinking moiety and wherein the crosslinking moiety is formed from a reaction between a boronic acid moiety and a hydroxamic acid moiety.

DESCRIPTION OF THE INVENTION

It is an object of the present invention to provide a hydrogel having a glycosaminoglycan (GAG) as the swellable polymer, having reversible linkages.

It is also an object of the present invention to provide a method for preparing hydrogels of glycosaminoglycan molecules by mild and efficient routes. It is also an object of the invention to provide a more facile and convenient method for manufacturing crosslinked glycosaminoglycans, with gel properties when dissolved in an aqueous liquid.

One object of the invention is to provide crosslinked glycosaminoglycans with less chemical modifications and/or a simpler structure.

Yet another object of the invention is to mitigate, alleviate or eliminate one or more of the drawbacks of the prior art.

The present invention concerns new hydrogel which show the following benefits:
Easier to inject,
More malleable,
can self-repair.

The invention concern also the use of such gels, of particular interest to fill wrinkles and/or shape the face more accurately and with fewer traumas for (the) patient.

In one aspect of the invention, there is provided, crosslinked glycosaminoglycans, wherein said glycosaminoglycans are crosslinked via an alkoxyboronate ester anion formed between a diol portion of a diol-functional moiety grafted to a first glycosaminoglycan and a boronate hemiester grafted to a second glycosaminoglycan. Crosslinked glycosaminoglycans according to the invention forms gel with higher storage (elastic) modulus compared to using phenylboronic acid as a crosslinker due to additional crosslinks formed between the boronate hemiester and the glycosaminoglycan hydroxyl groups (see example 10). Crosslinked glycosaminoglycans according to the invention further provide self-healing properties to the obtained gel (see e.g. FIG. 5, Example 30). The obtained gel is also easy to inject as the reversible bonds break when pushed through the syringe, and then quickly reform inside the body. The gels can be injected as preformed solids, because the solid gel can manage external damages and repair itself under a proper shear stress. Due to fast gelation kinetics after extrusion/injection, they recover their solid form almost immediately. Thus, before the gel reforms inside the body, the gel is malleable, until the reversible bonds reform. Thus, in one embodiment, the method provides a self-healing gel. The crosslinked glycosaminoglycans may optionally be further crosslinked.

A diol portion according to the invention may be any group comprising a diol, such as a 1,2-diol or a 1,3-diol. In certain embodiments of the invention, the diol portion is a vicinal diol. In other embodiments of the invention, the diol portion is not a vicinal diol.

Typically, the diol portion is a sugar moiety or a derivative thereof. Suitable sugar derivatives are derivatives suitable for binding to a glycosaminoglycan. Such derivatives may be a mono- or di-saccharide-disulfide or an aminosugar.

As used herein, the term "boronate hemiester" is to be interpreted as a compound of general formula BR(OR)(OH), as opposed to a boronic acid, which has a general formula BR(OH)$_2$, or a boronate ester which has a general formula BR(OR)$_2$. Each R, in this context, may independently represent any organic moiety since the purpose of these formulae relates to different boron functional groups.

A boronate ester is in equilibrium with its tetrahedral anionic form in water (below). The anionic form is an hydroxyboronate ester anion (Hall, D. G., 2011, Boronic Acids: Preparation and Applications in Organic Synthesis, Medicine and Materials, Second Edition, Wiley-VCH Verlag GmbH & Co.).

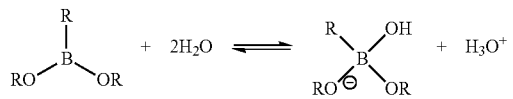

Thus, in general terms, an "alkoxyboronate ester anion" is to be understood as an anionic tetrahedral form, formed between a boronate ester and any alkoxy group, substituted or unsubstituted. An "alkoxyboronate ester anion" according to the invention, is an "alkoxyboronate ester anion" formed between a boronate hemiester and a diol portion of a diol-functional moiety grafted to glycosaminoglycan (below).

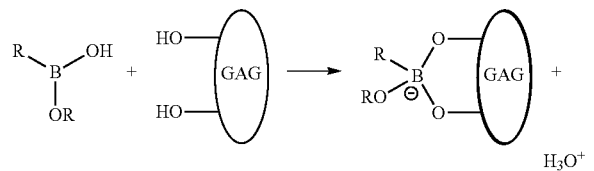

In one embodiment of this aspect of the invention the boronate hemiester is a compound comprising a 5-6-membered cyclic boronate hemiester moiety, sometimes referred to as a boroxole (Kotsubayashi et al. ACS Macro Lett. 2013, 2, 260-264). A five-membered boroxole is referred to as an oxaborole and a six-membered, an oxaborinine, see below. Thus, in one embodiment of this aspect of the invention the boronate hemiester is a compound comprising an oxaborole or an oxaborinine moiety. Glycosaminoglycans crosslinked by mixing a glycosaminoglycan grafted with a boroxole with a glycosaminoglycan grafted with a diol functional moiety is shown in the appended examples (e.g. Example 29) to give rise to a self-healing gel with improved pH stability as compared to the prior art. This provides for facilitated, more versatile and improved injection properties.

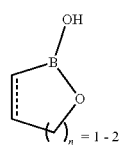

The present invention proposes new hydrogels:
in which the glycosaminoglycan chains are only connected with reversible crosslinks and which are based on mixtures of GAG-boroxole and a GAG-polyol derivative.

In one embodiment of this aspect of the invention the boronate hemiester is an optionally substituted benzoxaborole or benzoxaborinine. Benzoxaborole is sometimes referred to as benzoboroxole and the names may be used interchangeably (US 2014/0155305) The benzylic position of the boron atom in an optionally substituted benzoxaborole or benzoxaborinine stabilizes the empty p-orbital on the boron atom. Typically, the benzoxaborole or benzoxaborinine may be substituted with one or more of H, F, Cl, NO$_2$, C$_1$-C$_3$alkyl, C$_1$-C$_3$haloalkyl, C$_1$-C$_3$alkoxy, C$_3$-C$_6$cycloalkyl, phenyl, and a five- to six-membered heteroaromatic ring comprising 1 to 3 heteroatoms selected from O, N and S.

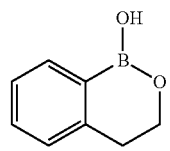
benzoxaborinine

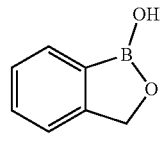
benzoxaborole

In one embodiment of this aspect of the invention, said crosslinked glycosaminoglycans has a structure of Formula (I)

I

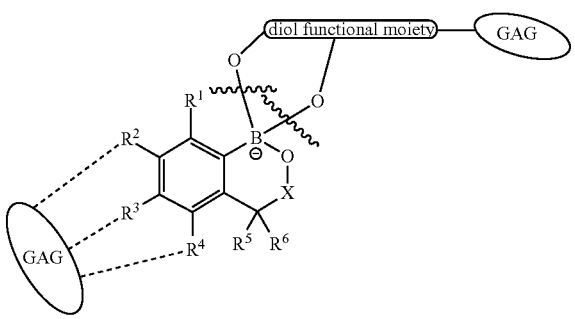

such as

I

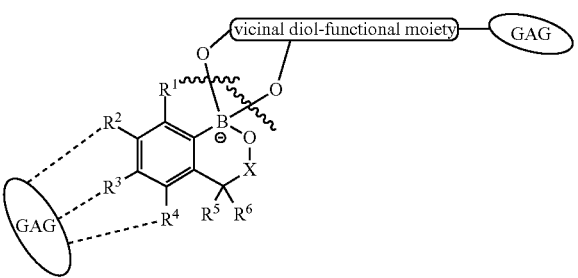

wherein
$R^1$ is selected from H, F, Cl, $NO_2$, $C_1$-$C_3$alkyl, $C_1$-$C_3$haloalkyl and $C_1$-$C_3$alkoxy;
$R^2$, $R^3$ and $R^4$ are independently selected from H, F, Cl, $C_1$-$C_3$haloalkyl, $NO_2$, $C_1$-$C_3$alkoxy, $C_1$-$C_3$alkyl and a linker, said linker binding covalently to said second glycosaminoglycan;
X is selected from $CHR^7$ and a bond;
$R^5$, $R^6$ and $R^7$ are independently selected from H, $C_1$-$C_4$alkyl, $C_3$-$C_6$cycloalkyl, phenyl, and a five- to six-membered heteroaromatic ring comprising 1 to 3 heteroatoms selected from O, N and S; and
wherein one of $R^2$, $R^3$ and $R^4$ is a linker. Using different substitution patterns on the boronate hemiester tune the characteristics of a gel formed between a diol portion of a diol-functional moiety grafted to a first glycosaminoglycan and a boronate hemiester grafted to a second glycosaminoglycan. Such characteristics may include improved stability, altered texture specifically advantageous for certain applications, or stability towards autoclavation. The benzylic carbon is a position where different substituents may give slightly different properties of the gel formed by compound of Formula (I). Thus, this gives an opportunity to finely tune the properties of the gel for different applications such as for imitating different tissues.

In certain embodiments of this aspect of the invention, the diol portion is a vicinal diol. In other embodiments of this aspect of the invention, the diol portion is not a vicinal diol.

As used herein, the term "$C_1$-$C_3$haloalkyl" means both linear and branched chain saturated hydrocarbon groups, with 1 to 3 carbon atoms and with 1 to all hydrogens substituted by a halogen of different or same type. Examples of $C_1$-$C_3$haloalkyl groups include methyl substituted with 1 to 3 halogen atoms, ethyl substituted with 1 to 5 halogen atoms, and n-propyl or iso-propyl substituted with 1 to 7 halogen atoms.

As used herein, the term "$C_1$-$C_3$fluorooalkyl" means both linear and branched chain saturated hydrocarbon groups, with 1 to 3 carbon atoms and with 1 to all hydrogen atoms substituted by a fluorine atom. Examples of $C_1$-$C_3$fluoroalkyl groups include methyl substituted with 1 to 3 fluorine atoms, ethyl substituted with 1 to 5 fluorine atoms, and n-propyl or iso-propyl substituted with 1 to 7 fluorine atoms.

The present disclosure provides new hydrogel products and related advantageous processes for preparing hydrogels made of crosslinked glycosaminoglycan (GAG) molecules having reversible linkages, and uses thereof. Glycosaminoglycans are negatively charged heteropolysaccharide chains which have a capacity to absorb large amounts of water. In the hydrogel products according to the disclosure, the crosslinked glycosaminoglycan molecule is the swellable polymer which provides the gel properties.

According to some embodiments, the glycosaminoglycan is selected from the group consisting of sulfated or non-sulfated glycosaminoglycans such as hyaluronan, chondroitin, chondroitin sulphate, heparan sulphate, heparosan, heparin, dermatan sulphate and keratan sulphate. According to some embodiments, the glycosaminoglycan is selected from the group consisting of hyaluronic acid, chondroitin and chondroitin sulfate, and mixtures thereof.

In one embodiment of this aspect of the invention, said glycosaminoglycans are hyaluronic acid. Hyaluronic acid (HA) is one of the most widely used biocompatible polymers for medical and cosmetic use. HA is a naturally occurring polysaccharide belonging to the group of glycosaminoglycans (GAGs). Hyaluronic acid consists of two alternating monosaccharides units, N-acetyl-D-glucosamine (GlcNAc) and D-glucuronic acid (GlcA), assembled by β(1→3) and β(1→4) glycosidic bonds, respectively. Hyaluronic acid and products derived from hyaluronic acid are widely used in the biomedical and cosmetic fields, for instance during viscosurgery and as a dermal filler.

Crosslinking of hyaluronic acid may be achieved by modification with a boroxole derivative and a polyol derivative to form linear HA-BOR and HA-polyol derivatives. The degree of substitution (DS) of these HA-conjugates can be varied in a range from 0.05 to 0.70 in order to tune the rheological behavior of the gels.

Unless otherwise specified, the term "hyaluronic acid" encompasses all variants and combinations of variants of hyaluronic acid, hyaluronate or hyaluronan, of various chain lengths and charge states, as well as with various chemical modifications. That is, the term also encompasses the various hyaluronate salts of hyaluronic acid with various counter ions, such as sodium hyaluronate. The hyaluronic acid can be obtained from various sources of animal and non-animal origin. Sources of non-animal origin include yeast and preferably bacteria. The molecular weight of a single hyaluronic acid molecule is typically in the range of 0.1-10 kg/mol, but other molecular weights are possible. According to the invention, preferred molecular weights are in the range 50-3000 kg/mol, more preferably in the range 70-1000 kg/mol.

In one embodiment of this aspect of the invention, the molecular weight of the glycosaminoglycan is between 200-1500 kg/mol, preferably in the range 400-1100 kg/mol, more preferably 500-1000 kg/mol, more preferably 600-800 kg/mol.

In one embodiment of this aspect of the invention, the molecular weight of the glycosaminoglycan is between 50-1000 kg/mol, such as 50-500 kg/mol, such as 50-200 kg/mol, such as around 100 kg/mol.

In one embodiment of this aspect of the invention, the degree of substitution of the glycosaminoglycans is 0.05-0.3, preferably 0.1-0.2.

In one embodiment of this aspect of the invention, the degree of substitution of the glycosaminoglycans is 0.05-0.7, preferably 0.1-0.6, more preferably 0.15-0.5. It has been experimentally observed that these ranges of degree of substitution of the hyaluronic acid with a boronate hemiester and subsequently mixed with a glycosaminoglycan grafted with a diol functional moiety exhibit improved gel properties (e.g. G' and G"). The degree of substitution may be measured on the substituted polymer glycosaminoglycans by NMR.

The term "chondroitin" refers to glycosaminoglycans having a disaccharide repeating unit consisting of alternating non-sulfated D-glucuronic acid and N-acetyl-D-galactosamine moieties. For avoidance of doubt, the term "chondroitin" does not encompass any form of chondroitin sulfate.

The term "chondroitin sulfate" refers to glycosaminoglycans having a disaccharide repeating unit consisting of alternating D-glucuronic acid and N-acetyl-D-galactosamine moieties. The sulfate moiety can be present in various different positions. Preferred chondroitin sulfate molecules are chondroitin-4-sulfate and chondroitin-6-sulfate.

The chondroitin molecules can be obtained from various sources of animal and non-animal origin. Sources of non-animal origin include yeast and preferably bacteria. The molecular weight of a single chondroitin molecule is typically in the range of 1-500 kg/mol, but other molecular weights are possible.

The term "crosslinked glycosaminoglycans" or "crosslinked glycosaminoglycan molecules" refers herein to glycosaminoglycans comprising, typically covalent, crosslinks between the glycosaminoglycan molecule chains, which creates a continuous network of glycosaminoglycan molecules held together by the crosslinks.

The crosslinked glycosaminoglycan product is preferably biocompatible. This implies that no, or only very mild, immune response occurs in the treated individual. That is, no or only very mild undesirable local or systemic effects occur in the treated individual.

The crosslinked product according to the disclosure is a gel, or a hydrogel. That is, it can be regarded as a water-insoluble, but substantially dilute crosslinked system of glycosaminoglycan molecules when subjected to a liquid, typically an aqueous liquid.

In one embodiment of this aspect of the invention, said linker forms an amide bond or an ether bond with said second glycosaminoglycan; According to this embodiment, the linker forms an amide bond or an ether bond, respectively, with the backbone of said second glycosaminoglycan. Thus self-healing crosslinked glycosaminoglycans are achieved with less modified glycosaminoglycans. By having the linker of the boronate hemiester bound by an amide bond or an ether bond provides for stable gel as ethers and amides are both stable to physiological conditions. The grafting of a compound of Formula I to said second glycosaminoglycan may be done for example via an ether bond by reacting for example a hydroxy group of the backbone of the glycosaminoglycan with an epoxy functionality of said linker. The grafting of the compound of Formula I to said second glycosaminoglycan may also be done by using 4-(4,6-dimethoxy-1,3,5-triazin-2-yl)-4-methylmorpholinium chloride (DMTMM) to activate carboxylic groups on said second glycosaminoglycan and react the resulting species with an amine function of said linker to form a stable amide. Thus, a self-healing gel with a less modified glycosaminoglycan in obtained.

In one embodiment of this aspect of the invention, said linker is —NR$^9$—Y— or —O—Y— and forms an amide bond or an ether bond with said second glycosaminoglycan, wherein R$^9$ is selected from hydrogen, $C_1$-$C_3$alkyl and $C_1$-$C_3$fluoroalkyl;

Y is selected from a bond and $C_1$-$C_6$alkylene in which one or two $CH_2$ are optionally replaced by a group selected from O, NH and phenylene, said $C_1$-$C_6$alkylene being optionally substituted with 1 to 12 R$^8$; and R$^8$ is selected from F, Cl, $C_1$-$C_3$alkyl, $C_1$-$C_3$haloalkyl, phenyl, OH, $C_1$-$C_3$hydroxyalkyl, $C_1$-$C_3$alkoxy, NH$_2$, N—$C_1$-$C_3$alkylamino, N—N—$C_1$-$C_4$dialkylamino.

In one embodiment of this aspect of the invention, R$^2$ is a linker. As used herein, a linker is a moiety of a molecule that links it to another molecule. Thus, inherent in the term "linker" is that a linker has a portion which is capable of binding to another molecule, preferably directly to the other molecule. Such binding portion may be for example an amine group, a hydroxy group, or an alkene. A linker in the sense of the invention is the portion of the boronate hemiester that links it to a glycosaminoglycan. Thus, the linker preferably leads to a stable binding to the glycosaminoglycan.

In one embodiment of this aspect of the invention, said linker is —NR$^9$—Y— and forms an amide bond with said second glycosaminoglycan, wherein R$^9$ is selected from hydrogen, $C_1$-$C_3$alkyl and $C_1$-$C_3$fluoroalkyl; and wherein Y is a bond or an unsubstituted $C_1$-$C_6$alkylene. By having the linker of the boronate hemiester bound by an amide bond provides for stable gel as amides are stable to physiological conditions. In known crosslinked glycosaminoglycans using boron chemistry, aminophenylboronic acid was bound to hyaluronic acid via a 5-(3-amino-3-oxo-propyl)sulfanylpentanoate moiety. According to the invention, the amine (or aniline) of the compound of Formula I may be bound directly to the backbone of said second glycosaminoglycan, for example by using 4-(4,6-dimethoxy-1,3,5-triazin-2-yl)-4-methylmorpholinium chloride (DMTMM) to activate carboxylic groups on said second glycosaminoglycan and react the resulting species with an amine function of said linker to form a stable amide Thus, a self-healing gel with a less modified glycosaminoglycan in obtained.

In one embodiment of this aspect of the invention, the boronate hemiester is

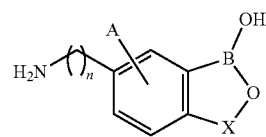

wherein A is selected from H, F, CF$_3$, NO$_2$, OCH$_3$ and CH$_3$;

n is selected from 0, 1, 2 and 3; and

X is selected from CH$_2$, CH$_2$—CH$_2$, CH—NC$_5$H$_{11}$ (CH-piperidine) and C(CH$_3$)$_2$.

In one embodiment of this aspect of the invention, R$^1$, R$^3$ and R$^4$ are independently selected from H, F, OCH$_3$, CF$_3$ and CH$_3$;

R$^2$ is a linker;

said linker is —HN—Y— and forms an amide bond with said second glycosaminoglycan;

Y is a bond or unsubstituted $C_1$-$C_3$alkylene;
X is a bond or $CH_2$; and
$R^5$ and $R^6$ are independently selected from H and $C_1$-$C_3$alkyl. X has two connections and the term $CH_2$ thus means methylene or —$CH_2$—.

In one embodiment of this aspect of the invention,
$R^1$ is selected from H, F and $OCH_3$;
$R^2$ is a linker;
$R^3$ and $R^4$ are hydrogen;
said linker is —HN— and forms an amide bond with said second glycosaminoglycan;
Y is a bond or an unsubstituted methylene;
X is a bond or $CH_2$; and
$R^5$ and $R^6$ are independently selected from H and $C_1$-$C_3$alkyl.

In one embodiment of this aspect of the invention, said boronate hemiester is selected from

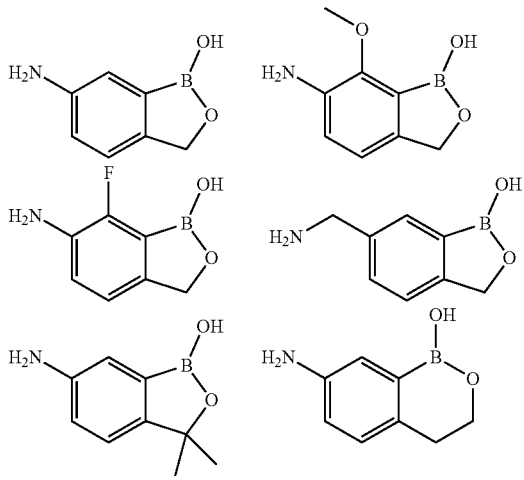

wherein the boronate hemiester is grafted to said second glycosaminoglycan by that the —$NH_2$ group of the boronate hemiester forms an amide with a backbone carboxylate group of said second glycosaminoglycan.

In one embodiment of this aspect of the invention, said boronate hemiester is selected from

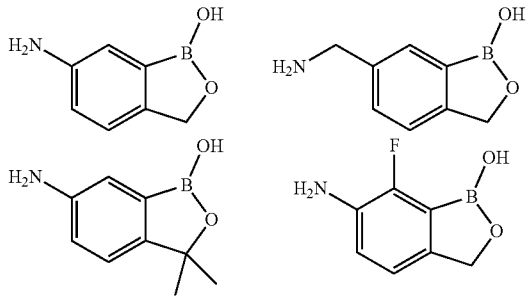

wherein the boronate hemiester is grafted to said second glycosaminoglycan by that the —$NH_2$ group of the boronate hemiester forms an amide with a backbone carboxylate group of said second glycosaminoglycan.

In certain embodiments of the invention the crosslinked glycosaminoglycans provide a gel that is stable to autoclavation, which gives a safer gel when used inside the body, such as for injection or when used in implants.

In one embodiment of this aspect of the invention, the crosslinked glycosaminoglycans having a structure of Formula (II)

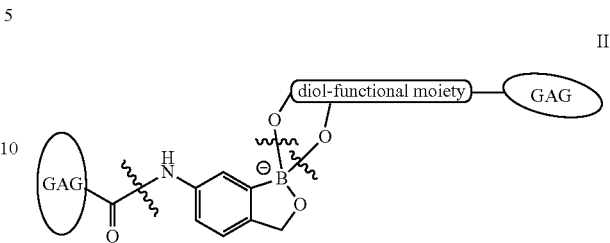

By crosslinking via an alkoxyboronate ester anion with a structure of Formula II, a more stable gel is obtained, particularly a more pH stable gel as is shown in example 29.

In certain embodiments of this aspect of the invention, the diol portion is a vicinal diol. In other embodiments of this aspect of the invention, the diol portion is not a vicinal diol.

In one embodiment of this aspect of the invention, said diol portion is selected from a monosaccharide, a disaccharide and an alditol or a derivative thereof. Typically, such diol portion is selected from a hexose, a dihexose and a $C_6$alditol or a derivative thereof. Such derivatives are derivatives which enable grafting to the glycosaminoglycan to which the diol portion is to be grafted. Such derivatives may be for example an aminosugar, a mono- or di-saccharide-sulfide or a sugar acid. Thus, the diol-functional moiety consists of a diol portion and a linking portion. Methods for linking a diol portion, such as a sugar derivative, to a glycosaminoglycan are known to a person skilled in the art.

In one embodiment of this aspect of the invention, said diol portion is selected from maltose, fructose, lactose and sorbitol or a derivative thereof. Suitable derivatives for are maltose, fructose, lactose and sorbitol derivatives suitable for binding to a glycosaminoglycan. Such derivatives may be a mono- or di-saccharide-disulfide or an aminosugar.

In one embodiment of the invention said diol portion is selected from Maltose-disulfide, Lactobionic-disulfide, 1-amino-1-deoxy-D-fructose and 1-amino-1-deoxy-D-sorbitol.

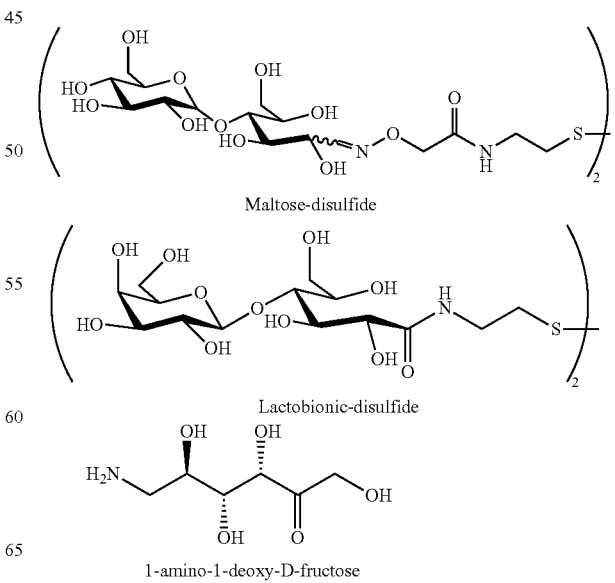

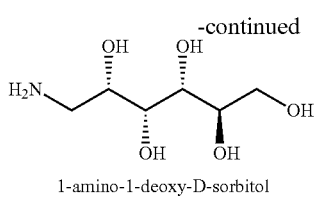

1-amino-1-deoxy-D-sorbitol

In one embodiment of this aspect of the invention, said diol portion is a ketose or a derivative thereof.

In one embodiment of this aspect of the invention, said diol portion is fructose or a derivative thereof.

In one aspect of the invention, there is provided, a method of crosslinking a first glycosaminoglycan grafted with a diol-functional moiety having a diol portion and a second glycosaminoglycan grafted with a boronate hemiester, comprising crosslinking said first glycosaminoglycan with said second glycosaminoglycan by forming an alkoxyboronate ester anion linkage between the boronate hemiester of said second glycosaminoglycan and the diol portion of said diol-functional moiety of said first glycosaminoglycan.

The method does not exclude additional crosslinking. A boronate hemiester has higher affinity towards diols than for example phenylboronic acid. Crosslinked glycosaminoglycans produced with a method according to the invention can form gels with higher storage (elastic) modulus compared to using phenylboronic acid as a crosslinker due to additional cross-links formed between the boronate hemiester and the glycosaminoglycan hydroxyl groups, as shown in example 10. In other words, a glycosaminoglycan can be grafted to a higher degree of substitution with a boronate hemiester than a corresponding glycosaminoglycan grafted with a phenylboronic acid. This is useful when forming a gel together with a glycosaminoglycan grafted with a diol-functional moiety, particularly a self-healing gel. The method according to the invention further provide self-healing properties to the obtained gel (see e.g. FIG. 5, Example 30). A gel produced by the method according to the invention is also easy to inject as the reversible bonds break when pushed through the syringe, and then quickly reform inside the body. The gels can be injected as preformed solids, because the solid gel can manage external damages and repair itself under a proper shear stress. Due to fast gelation kinetics after extrusion/injection, they recover their solid form almost immediately. Thus, before the gel reforms inside the body, the gel is malleable, until the reversible bonds reform. Thus, in one embodiment, the method provides a self-healing gel.

In one embodiment of this aspect of the invention the boronate hemiester is an optionally substituted benzoxaborole or benzoxaborinine. The benzylic position of the boron atom in an optionally substituted benzoxaborole or benzoxaborinine stabilizes the empty p-orbital on the boron atom. Typically, the benzoxaborole or benzoxaborinine may be substituted with one or more of H, F, Cl, NO$_2$, C$_1$-C$_3$alkyl, C$_1$-C$_3$haloalkyl, C$_1$-C$_3$alkoxy, C$_3$-C$_6$cycloalkyl, phenyl, and a five- to six-membered heteroaromatic ring comprising 1 to 3 heteroatoms selected from O, N and S. A benzoxaborole has higher affinity towards diols than for example phenylboronic acid. Crosslinked glycosaminoglycans produced with a method according to the invention can form gels with higher storage (elastic) modulus compared to using phenylboronic acid as a crosslinker due to additional cross-links formed between the boronate hemiester and the glycosaminoglycan hydroxyl groups, as shown in example 10. In other words, a glycosaminoglycan can be grafted to a higher degree of substitution with a benzoxaborole than a corresponding glycosaminoglycan grafted with a phenylboronic acid. This is useful when forming a gel together with a glycosaminoglycan grafted with a diol-functional moiety, particularly a self-healing gel.

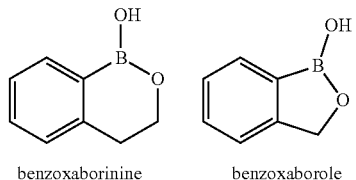

benzoxaborinine    benzoxaborole

In one embodiment of this aspect of the invention, the method further comprises, prior to the crosslinking step grafting said second glycosaminoglycan with said boronate hemiester, said boronate hemiester being a compound of Formula (III),

III

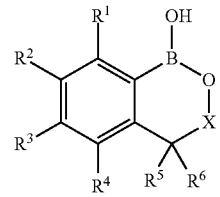

wherein
R$^1$ is selected from H, F, Cl, NO$_2$, C$_1$-C$_3$alkyl, C$_1$-C$_3$haloalkyl and C$_1$-C$_3$alkoxy; R$^2$, R$^3$ and R$^4$ are independently selected from H, F, Cl, C$_1$-C$_3$haloalkyl, NO$_2$, C$_1$-C$_3$alkoxy, C$_1$-C$_3$alkyl and a linker binding covalently to said second glycosaminoglycan;
X is selected from CHR$^7$ and a bond; and
R$^5$, R$^6$ and R$^7$ are independently selected from H, C$_1$-C$_4$alkyl, C$_3$-C$_6$cycloalkyl, phenyl, and a five- to six-membered heteroaromatic ring comprising 1 to 3 heteroatoms selected from O, N and S, wherein one of R$^2$, R$^3$ and R$^4$ is a linker.

In one embodiment of this aspect of the invention, said first and said second glycosaminoglycans are hyaluronic acid.

In one embodiment of this aspect of the invention, the molecular weight of the glycosaminoglycan is between 200-1500 kg/mol, preferably in the range 400-1100 kg/mol, more preferably 500-1000 kg/mol, more preferably 600-800 kg/mol.

In one embodiment of this aspect of the invention, the molecular weight of the glycosaminoglycan is between 50-1000 kg/mol, such as 50-500 kg/mol, such as 50-200 kg/mol, such as around 100 kg/mol.

In one embodiment of this aspect of the invention, the degree of substitution of the glycosaminoglycans is 0.05-0.3, preferable 0.1-0.2.

In one embodiment of this aspect of the invention, the degree of substitution of the glycosaminoglycans is 0.05-0.7, preferably 0.1-0.6, more preferably 0.15-0.5. It has been experimentally observed that these ranges of degree of substitution of the hyaluronic acid with a boronate hemiester and subsequently mixed with a glycosaminoglycan grafted with a diol functional moiety exhibit improved gel properties (e.g. G' and G"). The degree of substitution may be measured on the substituted polymer glycosaminoglycans by NMR.

In one embodiment of this aspect of the invention, said linker forms an amide bond or an ether bond to said second glycosaminoglycan.

The grafting of the compound of Formula I to said second glycosaminoglycan may be done for example via an ether bond by reacting for example a hydroxy group of the backbone of the glycosaminoglycan with an epoxy functionality of said linker. The grafting of the compound of Formula I to said second glycosaminoglycan may also be done by using 4-(4,6-dimethoxy-1,3,5-triazin-2-yl)-4-methylmorpholinium chloride (DMTMM) to activate carboxylic groups on said second glycosaminoglycan and react the resulting species with an amine function of said linker to form a stable amide.

As used herein, the term "backbone" refers to the polysaccharide chain in its native form i.e. groups grafted to the backbone are not part of the backbone. As an example, below the backbone of hyaluronic acid is shown.

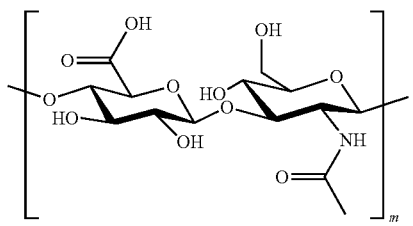

In one embodiment of this aspect of the invention, said linker is $H_2N-Y-$ or

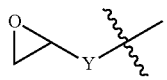

and forms an amide bond or an ether bond with said second glycosaminoglycan;

Y is selected from a bond and $C_1$-$C_6$alkylene in which one or two $CH_2$ are optionally replaced by a group selected from O, NH and phenylene, said $C_1$-$C_6$alkylene being optionally substituted with 1 to 12 $R^8$; and $R^8$ is selected from F, Cl, $C_1$-$C_3$alkyl, $C_1$-$C_3$haloalkyl, phenyl, OH, $C_1$-$C_3$hydroxyalkyl, $C_1$-$C_3$alkoxy, $NH_2$, N—$C_1$-$C_3$alkylamino, $C_4$dialkylamino.

In one embodiment of this aspect of the invention, $R^2$ is a linker.

In one embodiment of this aspect of the invention, said linker is $HR^9N-Y-$ and forms an amide bond with said second glycosaminoglycan, wherein $R^9$ is selected from hydrogen, $C_1$-$C_3$alkyl and $C_1$-$C_3$fluoroalkyl; and Y is a bond or an unsubstituted $C_1$-$C_6$alkylene. The grafting of the compound of Formula I to said second glycosaminoglycan may also be done by using 4-(4,6-dimethoxy-1,3,5-triazin-2-yl)-4-methylmorpholinium chloride (DMTMM) to activate carboxylic groups on said second glycosaminoglycan and react the resulting species with an amine function ($HR^9N-Y-$) of said linker to form a stable amide.

In one embodiment of this aspect of the invention, $R^9$ is hydrogen.

In one embodiment of this aspect of the invention, the boronate hemiester is

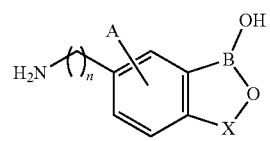

wherein A is selected from H, F, $CF_3$, $NO_2$, $OCH_3$ and $CH_3$;

n is selected from 0, 1, 2 and 3; and

X is selected from $CH_2$, $CH_2$—$CH_2$, CH—$NC_5H_{11}$ (CH-piperidine) and $C(CH_3)_2$.

In one embodiment of this aspect of the invention, $R^1$, $R^3$ and $R^4$ are independently selected from H, F, $OCH_3$, $CF_3$ and $CH_3$;

$R^2$ is a linker;

said linker is $H_2N-Y-$ and forms an amide bond with said second glycosaminoglycan;

Y is a bond or an unsubstituted $C_1$-$C_3$alkylene;

X is a bond or $CH_2$; and $R^5$ and $R^6$ are independently selected from H and $C_1$-$C_3$alkyl.

In one embodiment of this aspect of the invention, $R^1$ is selected from H, F and $OCH_3$;

$R^2$ is a linker;

$R^3$ and $R^4$ are hydrogen;

said linker is —HN— and forms an amide bond with said second glycosaminoglycan;

Y is a bond or an unsubstituted methylene;

X is a bond or $CH_2$; and $R^5$ and $R^6$ are independently selected from H and $C_1$-$C_3$alkyl.

In one embodiment of this aspect of the invention, said boronate hemiester is selected from

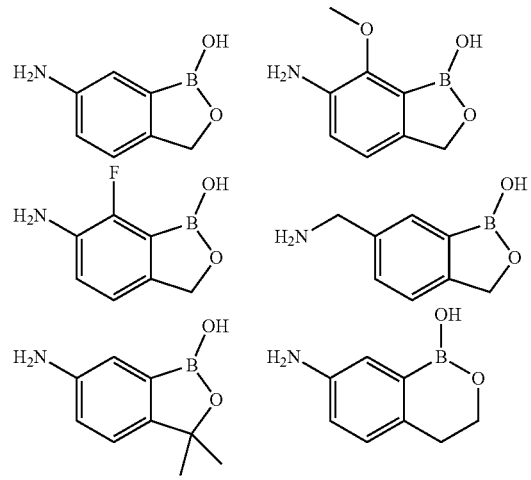

wherein the boronate hemiester is grafted to said second glycosaminoglycan by that the —$NH_2$ group of the boronate hemiester forms an amide with a backbone carboxylate group of said second glycosaminoglycan.

In one embodiment of this aspect of the invention, said boronate hemiester is selected from

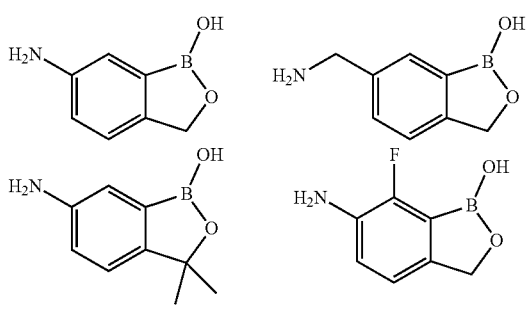

wherein the boronate hemiester is grafted to said second glycosaminoglycan by that the —NH$_2$ group of the boronate hemiester forms an amide with a backbone carboxylate group of said second glycosaminoglycan.

In one embodiment of this aspect of the invention, said boronate hemiester being

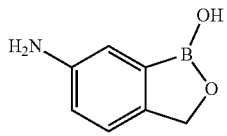 [SMILES: Nc1ccc2c(c1)B(O)OC2]

The compound above may be called 5-amino-2-hydroxymethylphenylboronic acid. According to the generated IUPAC name in Biovia DRAW 4.2, it should be named 1-hydroxy-3H-2,1-benzoxaborol-amine.

In one embodiment of this aspect of the invention, said diol portion is selected from a monosaccharide, a disaccharide and an alditol or a derivative thereof. Typically, such diol portion is selected from a hexose, a dihexose and a C$_6$alditol or a derivative thereof.

In one embodiment of this aspect of the invention, said diol portion is selected from maltose, fructose, lactose and sorbitol or a derivative thereof. Suitable derivatives are maltose, fructose, lactose and sorbitol derivatives suitable for binding to a glycosaminoglycan. Such derivatives may be a mono- or di-saccharide-disulfide or an aminosugar.

In one embodiment of the invention said diol portion is selected from Maltose-disulfide, Lactobionic-disulfide, 1-amino-1-deoxy-D-fructose and 1-amino-1-deoxy-D-sorbitol.

In one embodiment of this aspect of the invention, said diol portion is fructose or a derivative thereof.

In one aspect of the invention, there is provided, use of a boronate hemiester in the manufacture of crosslinked glycosaminoglycans, the crosslinkage being via an alkoxyboronate ester anion formed between a diol portion of a diol-functional moiety grafted to a first glycosaminoglycan and a boronate hemiester grafted to a second glycosaminoglycan. The use of a boronate hemiester to crosslink glycosaminoglycans, does not exclude that the glycosaminoglycans are further crosslinked. A boronate hemiester has higher affinity towards diols than for example phenylboronic acid. A boronate hemiester can form gels with higher storage (elastic) modulus compared to using phenylboronic acid as a crosslinker due to additional cross-links formed between the boronate hemiester and the glycosaminoglycan hydroxyl groups, as shown in example 10. In other words a glycosaminoglycan can be grafted to a higher degree of substitution with a boronate hemiester than a corresponding glycosaminoglycan grafted with a phenylboronic acid. This is useful when forming a gel together with a glycosaminoglycan grafted with a diol-functional moiety, particularly a self-healing gel. Thus, a boronate hemiester is a stronger reversible crosslinker. The use of a boronate hemiester in the manufacture of crosslinked glycosaminoglycans according to the invention further provide self-healing properties to the obtained gel (see e.g. FIG. 5, Example 30). The obtained gel is also easy to inject as the reversible bonds break when pushed through the syringe, and then quickly reform inside the body. The gels can be injected as preformed solids, because the solid gel can manage external damages and repair itself under a proper shear stress. Due to fast gelation kinetics after extrusion/injection, they recover their solid form almost immediately. Thus, before the gel reforms inside the body, the gel is malleable, until the reversible bonds reform. Thus, in one embodiment, the method provides a self-healing gel. The crosslinked glycosaminoglycans may optionally be further crosslinked.

In one embodiment of this aspect of the invention the boronate hemiester is an optionally substituted benzoxaborole or benzoxaborinine. The benzylic position of the boron atom in an optionally substituted benzoxaborole or benzoxaborinine stabilizes the empty p-orbital on the boron atom. Typically, the benzoxaborole or benzoxaborinine may be substituted with one or more of H, F, Cl, NO$_2$, C$_1$-C$_3$alkyl, C$_1$-C$_3$haloalkyl, C$_1$-C$_3$alkoxy, C$_3$-C$_6$cycloalkyl, phenyl, and a five- to six-membered heteroaromatic ring comprising 1 to 3 heteroatoms selected from O, N and S. A benzoxaborole has higher affinity towards diols than for example phenylboronic acid. Benzoxaborole or benzoxaborinine can form gels with higher storage (elastic) modulus compared to using phenylboronic acid as a crosslinker due to additional cross-links formed between the boronate hemiester and the glycosaminoglycan hydroxyl groups, as shown in example 10. In other words, glycosaminoglycan can be grafted to a higher degree of substitution with a benzoxaborole than a corresponding glycosaminoglycan grafted with a phenylboronic acid, particularly a self-healing gel.

In one embodiment of this aspect of the invention, said boronate hemiester is a compound of Formula (IV)

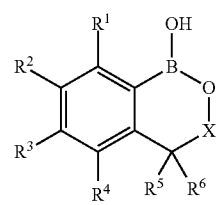

IV wherein
R$^1$ is selected from H, F, Cl, NO$_2$, C$_1$-C$_3$alkyl, C$_1$-C$_3$haloalkyl and C$_1$-C$_3$alkoxy;
R$^2$, R$^3$ and R$^4$ are independently selected from H, F, Cl, C$_1$-C$_3$haloalkyl, NO$_2$, C$_1$-C$_3$alkoxy, C$_1$-C$_3$alkyl and a linker capable of binding covalently to said second glycosaminoglycan;
X is selected from CHR$^7$ and a bond; and
R$^5$, R$^6$ and R$^7$ are independently selected from H, C$_1$-C$_4$alkyl, C$_3$-C$_6$cycloalkyl, phenyl, and a five- to six-membered heteroaromatic ring comprising 1 to 3 heteroatoms selected from O, N and S, wherein one of R$^2$, R$^3$ and R$^4$ is a linker. The benzylic position of the boron atom in a compound of Formula (IV) or in an optionally substituted benzoxaborole or benzoxaborinine stabilizes the empty p-orbital on the boron atom. The linker in position $R^2$, $R^3$ or $R^4$ is the group binding a compound of Formula (IV) to said second glycosaminoglycan and thus enables the grafting of said compound to said second glycosaminoglycan.

In one embodiment of this aspect of the invention, said glycosaminoglycans are hyaluronic acid.

In one embodiment of this aspect of the invention, the molecular weight of the glycosaminoglycan is between 200-1500 kg/mol, preferably in the range 400-1100 kg/mol, more preferably 500-1000 kg/mol, more preferably 600-800 kg/mol.

In one embodiment of this aspect of the invention, the molecular weight of the glycosaminoglycan is between 50-1000 kg/mol, such as 50-500 kg/mol, such as 50-200 kg/mol, such as around 100 kg/mol.

In one embodiment of this aspect of the invention, the degree of substitution of the glycosaminoglycans is 0.05-0.3, preferable 0.1-0.2. It has been experimentally observed that these ranges of degree of substitution of the hyaluronic acid with a boronate hemiester and subsequently mixed with a glycosaminoglycan grafted with a diol functional moiety exhibit improved gel properties (e.g. G' and G"). The degree of substitution may be measured on the substituted polymer glycosaminoglycans by NMR.

In one embodiment of this aspect of the invention, said linker is capable of forming an amide bond or an ether bond to said second glycosaminoglycan. According to this embodiment, the linker forms an amide bond or an ether bond, respectively, with the backbone of said second glycosaminoglycan. Forming an ether bond may be done by reacting for hydroxy group of the backbone of the glycosaminoglycan with an epoxy functionality of the linker. Forming an amide bond between a linker comprising an amine function and a glycosaminoglycan may be done by using 4-(4,6-dimethoxy-1,3,5-triazin-2-yl)-4-methylmorpholinium chloride (DMTMM) to activate carboxylic groups on the second glycosaminoglycan and react the resulting species with an amine function of said linker to form a stable amide. The use of a compound of Formula (IV) with a linker capable of forming an amide bond or an ether bond to said second glycosaminoglycan gives a more facile synthesis with fewer steps for grafting a boronate hemiester to a glycosaminoglycan.

In one embodiment of this aspect of the invention, $R^2$ is a linker.

In one embodiment of this aspect of the invention, said linker is $HR^9N$—Y— or

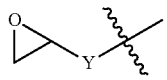

and capable of forming an amide bond or an ether bond with said second glycosaminoglycan, wherein $R^9$ is selected from hydrogen, $C_1$-$C_3$alkyl and $C_1$-$C_3$fluoroalkyl;
Y is selected from a bond and $C_1$-$C_6$alkylene in which one or two $CH_2$ are optionally replaced by a group selected from O, NH and phenylene, said $C_1$-$C_6$alkylene being optionally substituted with 1 to 12 $R^8$; and
$R^8$ is selected from F, Cl, $C_1$-$C_3$alkyl, $C_1$-$C_3$haloalkyl, phenyl, OH, $C_1$-$C_3$hydroxyalkyl, $C_1$-$C_3$alkoxy, $NH_2$, N—$C_1$-$C_3$alkylamino, $C_4$dialkylamino.

In one embodiment of this aspect of the invention, said linker is $HR^9N$—Y— and capable of forming an amide bond with said second glycosaminoglycan, wherein $R^9$ is selected from hydrogen, $C_1$-$C_3$alkyl and $C_1$-$C_3$fluoroalkyl; and Y is a bond or an unsubstituted $C_1$-$C_6$alkylene. According to this embodiment, the linker forms an amide bond with the backbone of said second glycosaminoglycan. Forming an amide bond between a $HR^9N$—Y-linker and a glycosaminoglycan may be done by using 4-(4,6-dimethoxy-1,3,5-triazin-2-yl)-4-methylmorpholinium chloride (DMTMM) to activate carboxylic groups on the second glycosaminoglycan and react the resulting species with an amine function ($HR^9N$—Y—) of said linker to form a stable amide. The use of a compound of Formula (IV) with a $HR^9N$—Y-linker gives a more facile synthesis with fewer steps for grafting a boronate hemiester to a glycosaminoglycan.

In one embodiment of this aspect of the invention, $R^9$ is hydrogen.

In one embodiment of this aspect of the invention, the boronate hemiester is

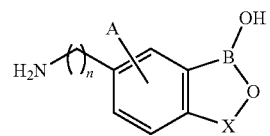

wherein A is selected from H, F, $CF_3$, $NO_2$, $OCH_3$ and $CH_3$;
n is selected from 0, 1, 2 and 3; and
X is selected from $CH_2$, $CH_2$—$CH_2$, CH—$NC_5H_{11}$ (CH-piperidine) and $C(CH_3)_2$.

In one embodiment of this aspect of the invention, $R^1$, $R^3$ and $R^4$ are independently selected from H, F, $CF_3$ and $CH_3$;
$R^2$ is a linker;
said linker is $H_2N$—Y— and capable of forming an amide bond with said second glycosaminoglycan;
Y is a bond or an unsubstituted $C_1$-$C_3$alkylene;
X is a bond or $CH_2$; and
$R^5$ and $R^6$ are independently selected from H and $C_1$-$C_3$alkyl.

In one embodiment of this aspect of the invention,
$R^1$ is selected from H, F and $OCH_3$;
$R^2$ is a linker;
$R^3$ and $R^4$ are hydrogen;
said linker is —HN— and forms an amide bond with said second glycosaminoglycan;
Y is a bond or an unsubstituted methylene;
X is a bond or $CH_2$; and
$R^5$ and $R^6$ are independently selected from H and $C_1$-$C_3$alkyl.

In one embodiment of this aspect of the invention, said boronate hemiester is selected from

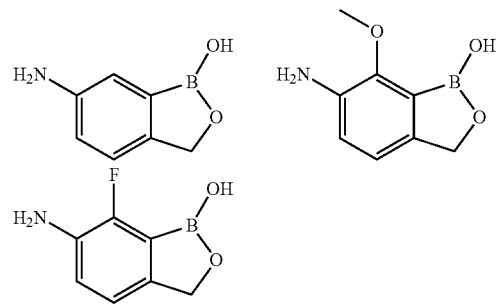

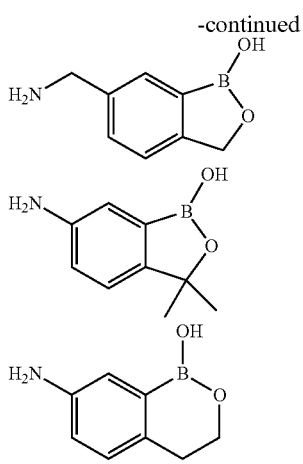

wherein the boronate hemiester is grafted to said second glycosaminoglycan by that the —NH₂ group of the boronate hemiester forms an amide with a backbone carboxylate group of said second glycosaminoglycan.

In one embodiment of this aspect of the invention, said boronate hemiester is selected from

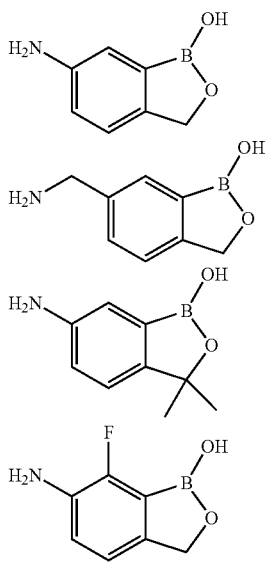

wherein the boronate hemiester is grafted to said second glycosaminoglycan by that the —NH₂ group of the boronate hemiester forms an amide with a backbone carboxylate group of said second glycosaminoglycan In one embodiment of this aspect of the invention, said boronate hemiester is

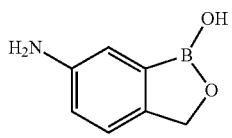

In one embodiment of this aspect of the invention, said diol portion is selected from a monosaccharide, a disaccharide and an alditol or a derivative thereof. Typically, such diol portion is selected from a hexose, a dihexose and a $C_6$alditol or a derivative thereof.

In one embodiment of this aspect of the invention, said diol portion is selected from maltose, fructose, lactose and sorbitol or a derivative thereof. Suitable derivatives for are maltose, fructose, lactose and sorbitol derivatives suitable for binding to a glycosaminoglycan. Such derivatives may be a mono- or di-saccharide-disulfide or an aminosugar.

In one embodiment of the invention said diol portion is selected from Maltose-disulfide, Lactobionic-disulfide, 1-amino-1-deoxy-D-fructose and 1-amino-1-deoxy-D-sorbitol.

In one embodiment of this aspect of the invention, said diol portion is a ketose or a derivative thereof.

In one embodiment of this aspect of the invention, said diol portion is a ketose or a derivative thereof.

In one embodiment of this aspect of the invention, said diol portion is fructose or a derivative thereof.

In one aspect of the invention, there is provided a polymer composition comprising crosslinked glycosaminoglycans according to the invention and an aqueous buffer. The polymer composition is optionally a self-healing hydrogel with higher degree of substitution than a gel based on phenylboronic acid crosslinking. The buffer is typically HEPES buffer. The crosslinked glycosaminoglycan product is preferably biocompatible. This implies that no, or only very mild, immune response occurs in the treated individual. That is, no or only very mild undesirable local or systemic effects occur in the treated individual.

The crosslinked product according to the disclosure is a gel, or a hydrogel. That is, it can be regarded as a water-insoluble, but substantially dilute crosslinked system of glycosaminoglycan molecules when subjected to a liquid, typically an aqueous liquid.

Crosslinked glycosaminoglycans produced according to the method according to the invention.

According to related aspects, the present disclosure also provides use of the hydrogel product as a medicament, such as in the treatment of soft tissue disorders. There is provided a method of treating a patient suffering from a soft tissue disorder by administering to the patient a therapeutically effective amount of the hydrogel product. There is also provided a method of providing corrective or aesthetic treatment to a patient by administering to the patient a therapeutically effective amount of the hydrogel product.

According to other aspects illustrated herein, there is provided a hydrogel product obtained by the inventive method for use as a medicament.

According to other aspects illustrated herein, there is provided a hydrogel product obtained by the inventive method for use in the treatment of soft tissue disorders.

According to other aspects illustrated herein, there is provided the use of a hydrogel product obtained by the inventive method for the manufacture of a medicament for treatment of soft tissue disorders.

According to other aspects illustrated herein, there is provided a method of treating a patient suffering from a soft tissue disorder by administering to the patient a therapeutically effective amount of a hydrogel product obtained by the inventive method.

According to other aspects illustrated herein, there is provided a method of providing corrective or aesthetic treatment to a patient by administering to the patient a therapeutically effective amount of a hydrogel product obtained by the inventive method.

According to other aspects illustrated herein, there is provided a method of cosmetically treating skin, which comprises administering to the skin a hydrogel product obtained by the inventive method.

Other aspects and preferred embodiments of the present invention will be evident from the appended examples.

The crosslinked glycosaminoglycan gel can be simply obtained from mixtures of HA-BOR/HA-polyol in a physiological buffer.

Due to its significant liquid content, the gel product is structurally flexible and similar to natural tissue, which makes it very useful as a scaffold in tissue engineering and for tissue augmentation. It is also useful for treatment of soft tissue disorder and for corrective or aesthetic treatment. It is preferably used as an injectable formulation.

The hydrogel product may be present in an aqueous solution, but it may also be present in dried or precipitated form, e.g. in ethanol.

The hydrogel product is preferably injectable.

The hyaluronic acid can be obtained from various sources of animal and non-animal origin. Sources of non-animal origin include yeast and preferably bacteria. The molecular weight of a single hyaluronic acid molecule is typically in the range of 0.1-10 kg/mol, but other molecular weights are possible.

In certain embodiments the concentration of said hyaluronic acid is in the range of 1 to 100 mg/ml. In some embodiments the concentration of said hyaluronic acid is in the range of 2 to 50 mg/ml. In specific embodiments the concentration of said hyaluronic acid is in the range of 5 to 30 mg/ml or in the range of 10 to 30 mg/ml). Crosslinked hyaluronic acid comprises crosslinks between the hyaluronic acid chains, which creates a continuous network of hyaluronic acid molecules which is held together by reversible covalent crosslinks.

A typical application of the resulting hydrogel product involves the preparation of injectable formulations for treatment of soft tissue disorders, including, but not limited to, corrective and aesthetic treatments.

The term "molecular weight" as used herein in connection with various polymers, e.g. polysaccharides, refers to the weight average molecular weight, $M_w$, of the polymers, which is well defined in the scientific literature. The weight average molecular weight can be determined by, e.g., static light scattering, small angle neutron scattering, X-ray scattering, and sedimentation velocity. The unit of the molecular weight for polymers is g/mol.

The person skilled in the art realizes that the present invention by no means is limited to the preferred embodiments described herein. On the contrary, many modifications and variations are possible within the scope of the appended claims. Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The derivatives of benzoboroxole acid selected consist of but, are not limited to compound of formula (I):

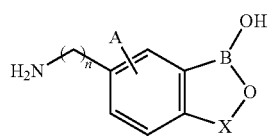

With A=H, F, $CF_3$, $NO_2$, $OCH_3$, $CH_3$ n=0, 1, 2 or 3

X=$CH_2$, $CH_2$—$CH_2$, CH—$NC_5H_{11}$ (CH-piperidine), $C(CH_3)_2$

The preferred derivatives of benzoboroxole is the benzoboroxole

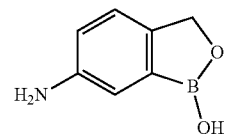

One object of the invention is a polymer composition comprising a mixture of:
a) Boroxole modified HA polymer grafted on at the carboxylate group with a group comprising boroxole, and
b) Polyol, preferably monosaccharide, disaccharide and diol modified HA, and more preferably mono-, disaccharide and cis-diol modified HA polymer grafted on at least a hydroxyl group or at the carboxylate group.

More specifically, polyols that can be used to form derivatives with HA are preferably fructose, maltose, glucose, lactose, mannose, galactose, sorbitol, or glycerol.

HA-Boroxole obtained is a compound of formula (III) as previously defined.

In one aspect of the invention, there is provided a, polymer composition comprising glycosaminoglycans (GAG) crosslinked by reversible boronate ester bonds.

In one embodiment of this aspect of the invention, said glycosaminoglycan is hyaluronic acid (HA)

In one embodiment of this aspect of the invention, the boroxole (BOR) modified hyaluronic acid (HA) is a polymer grafted at the carboxylate group comprising boroxole.

In one embodiment of this aspect of the invention, the compositions comprises a mixture of:
a) polymer grafted at the carboxylate group comprising boroxol; and
b) polyol modified hyaluronic acid (HA) polymer grafted on at least a hydroxyl with a group comprising a polyol.

In one embodiment of this aspect of the invention, the polymer composition comprises hyaluronic acid, wherein the polymer comprises doubly crosslinking based on biopolymer combining covalent ether bonds and reversible ester bonds, wherein, the stable covalent ether bonds is carried out between hydroxyl group of hyaluronic acid with 1,4-butanediol diglycidyl ether (BDDE), and wherein the reversible ester bonds are formed between benzoboroxole modified hyaluronic acid and polyols modified hyaluronic acid.

In one embodiment of this aspect of the invention, the compositions comprises a mixture of:
a) iminodiacetic acid (IDA) or diethanolamine (DEA) modified HA polymer grafted on at least a hydroxyl or at the carboxylate group with a group comprising na IDA or DEA derivative,
b) phenylboronic acid (PBA) or boroxole modified HA polymer grafted at the carboxylate comprising a boroxole or PBA derivative, HA-BOR
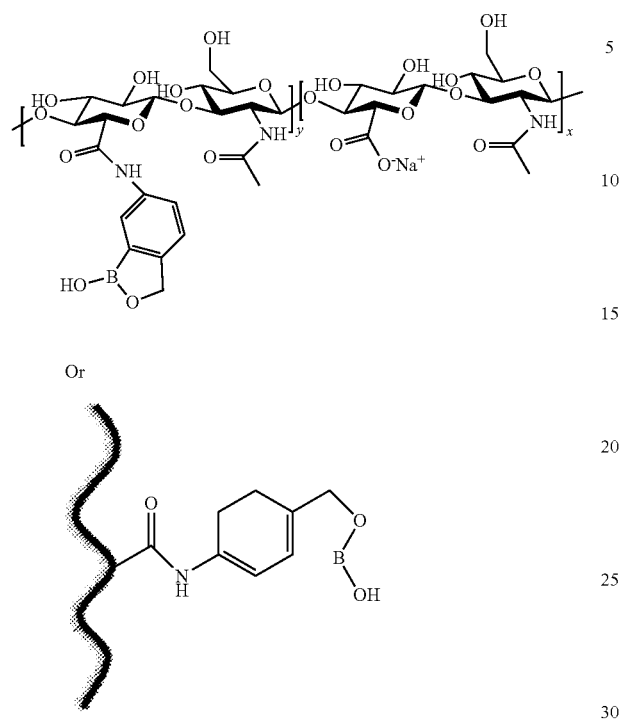
Or
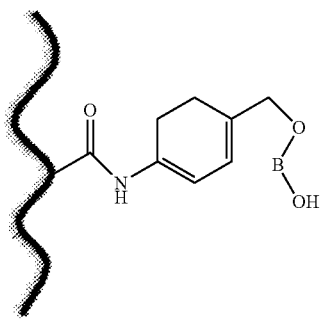
The polyols selected consist preferably of: Maltose, Lactose, Fructose and Sorbitol.
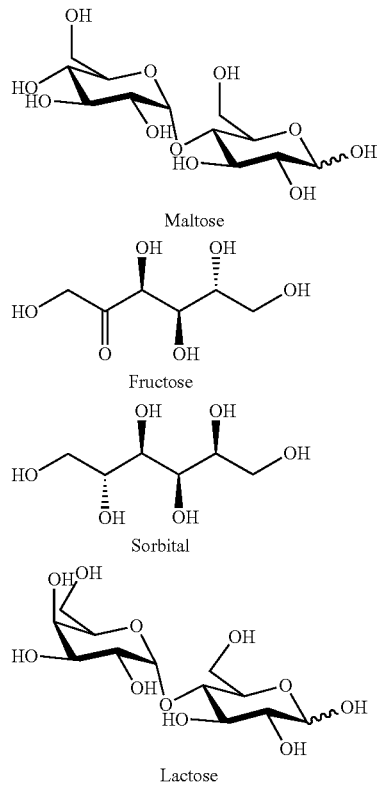
HA-polyols obtained are, as examples:
Ha-Maltose:
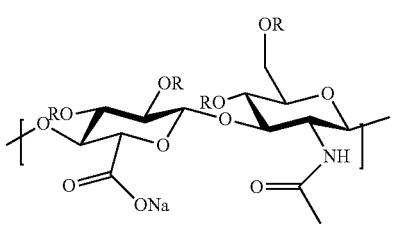
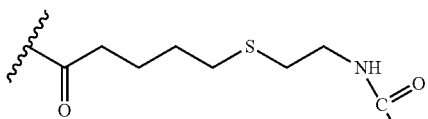
R=H or
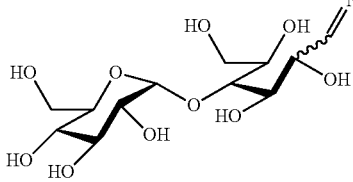
Ha-Fructose:
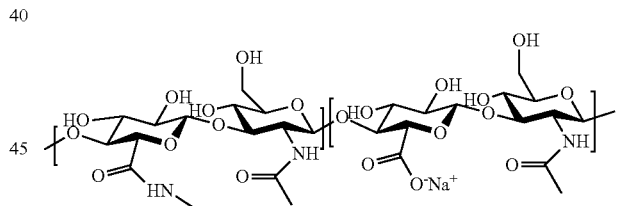
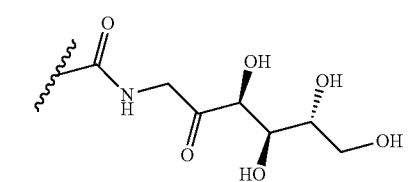
or Ha-Sorbitol:

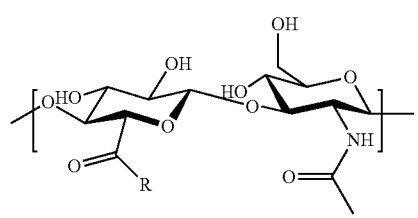

R = O⁻Na⁺ or

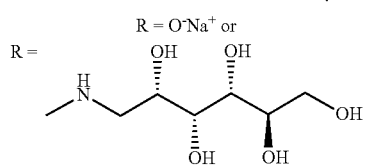

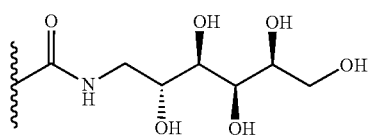

HA-lactose

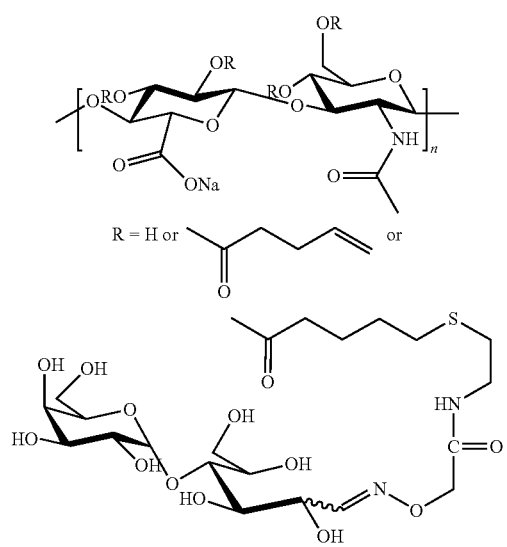

R = H or

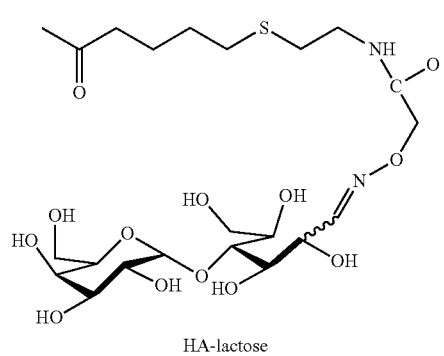

HA-lactose

The hydrogel combining HA-BOR and HA-polyols obtained according to the invention is, for example:

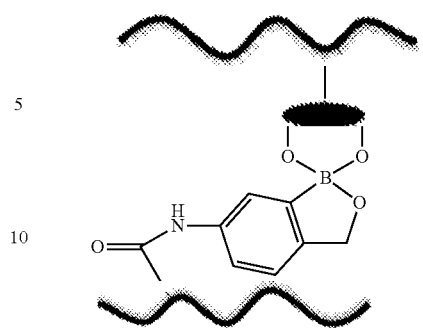

In the text of the present application, this symbol ● represents the polyol.

Figure 1A:
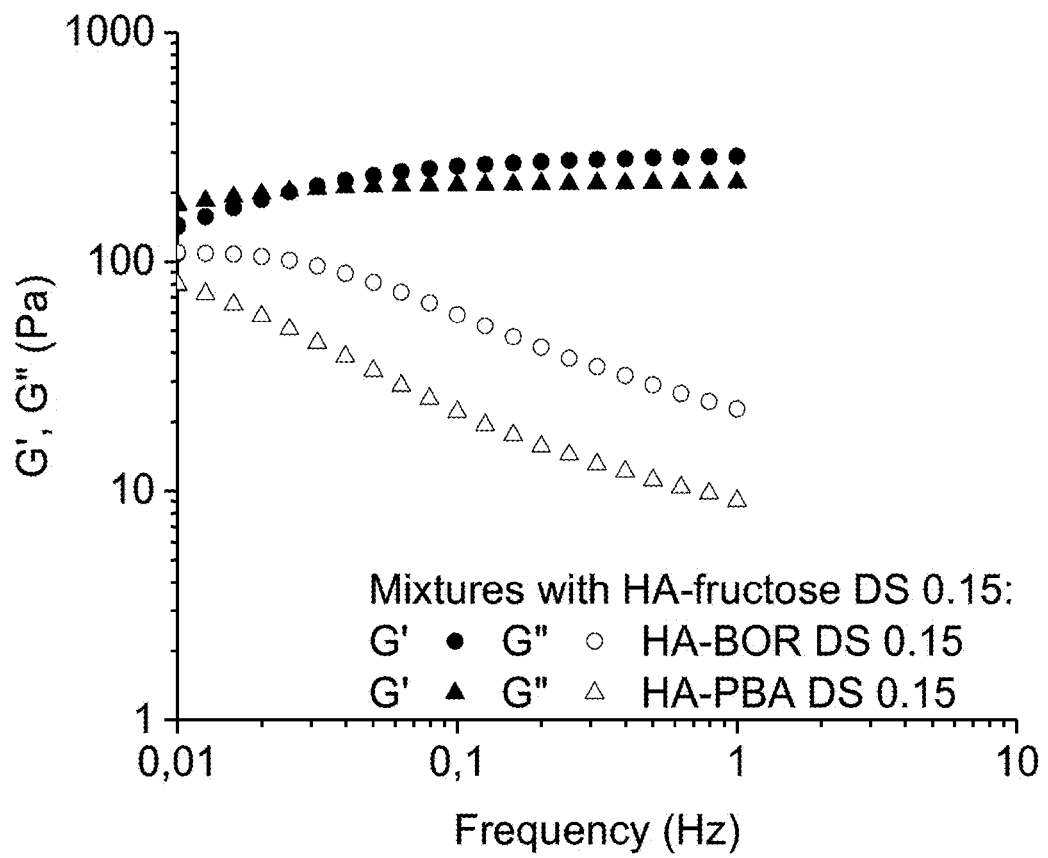
FIGS. 1A-1D: Rheological analyses of HA-BOR/HA-fructose and HA-PBA/HA-fructose mixtures in 0.01M HEPES buffer containing 0.15M NaCl at pH 7.4, using HA-BOR and HA-PBA with DS of 0.15 (A) and with higher DS of 0.4 and 0.5, respectively (B). Viscosity measurements of the HA-BOR and HA-PBA derivatives alone with DS of 0.15 (C) and with higher DS of 0.4 and 0.5, respectively (D).
Figure 1B:
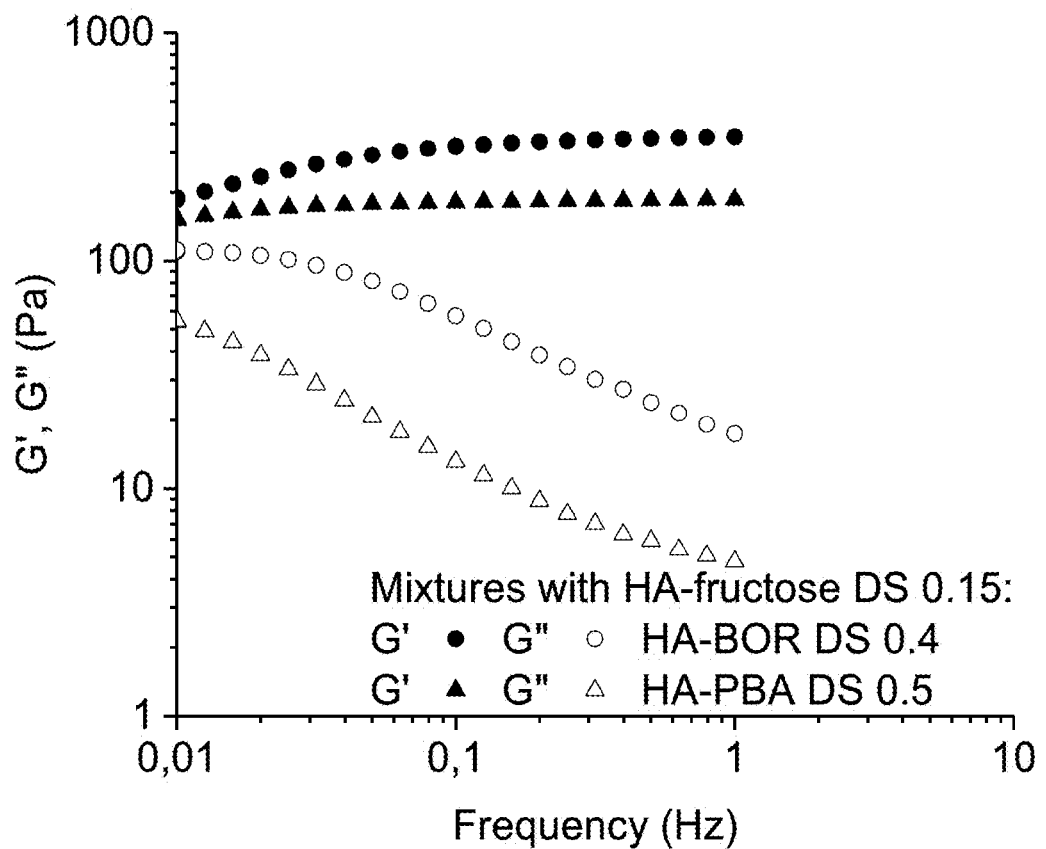
Figure 1C:
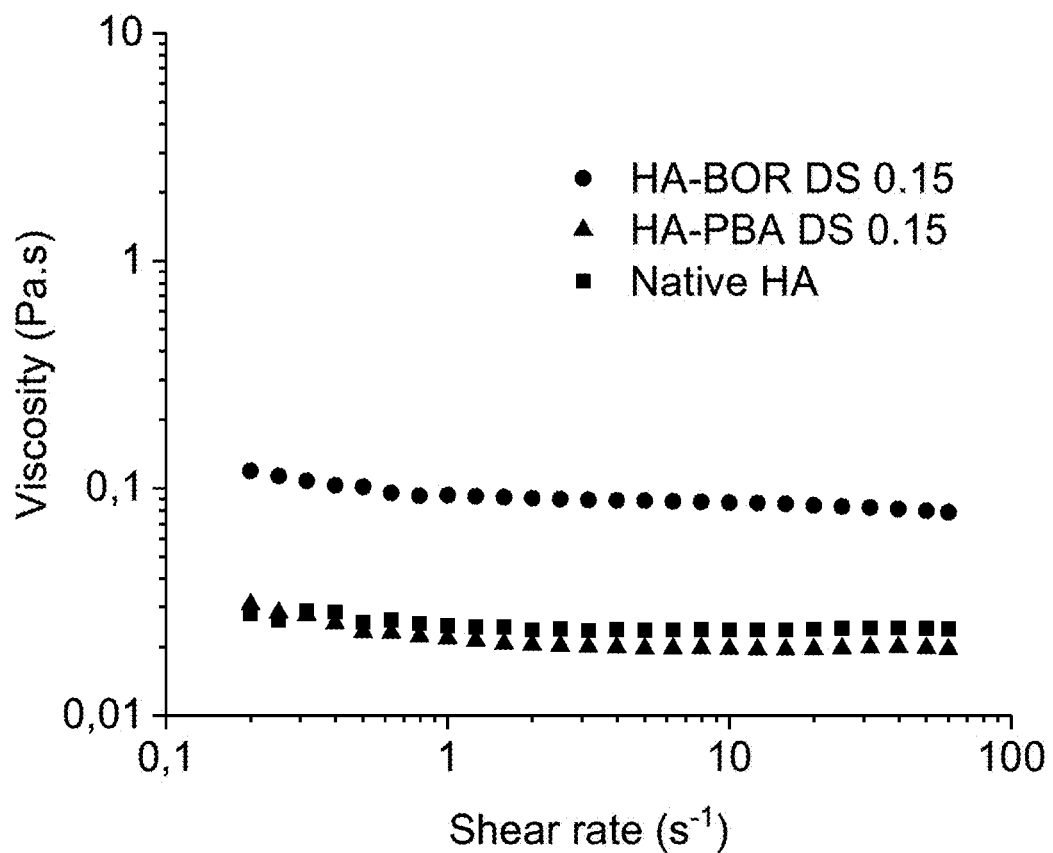
Figure 1D:
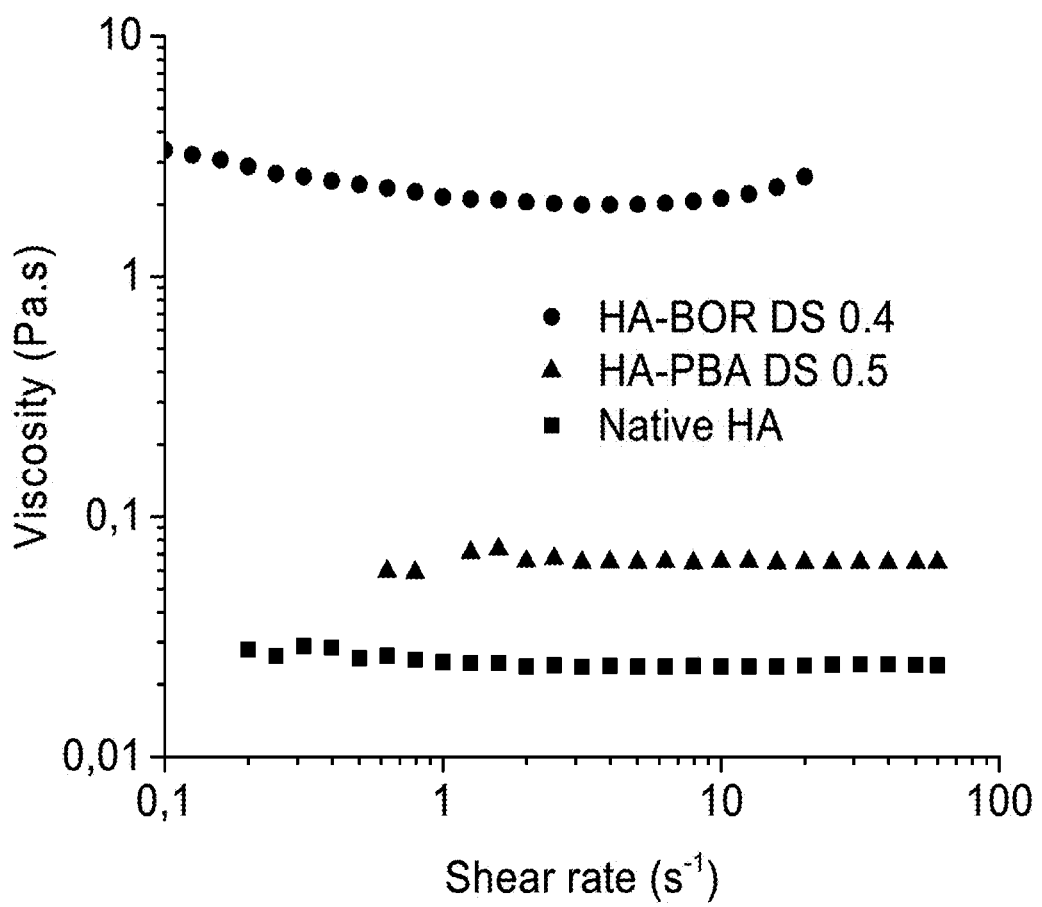

The following terms and characteristics will be used in the examples and results shown. The definitions are the one hereafter:

Mw—Molecular Weight: The mass average molecular mass

DS—Degree of Substitution The term "degree of substitution" (DS) as used herein in connection with various polymers, e.g. polysaccharides, refers to the average number of substituting group per repeating disaccharide unit.

[PS]—The polysaccharide concentration (g/l).

G': storage (elastic) modulus (in Pa)

G": loss (viscous) modulus (in Pa)

G' 1 Hz: storage modulus (in Pa) measured at a frequency of 1 Hz

G" 1 Hz: loss modulus (in Pa) measured at a frequency of 1 Hz

Gel-like behavior: G'>G" within the whole range of frequency covered (0.01-10 Hz)

Viscoelastic behavior: viscous (G'<G") and elastic (G'>G") behavior observed within the range of frequency covered (0.01-10 Hz).

The IUPAC names of the benzoboroxol derivatives in example 4-11 are generated using Biovia DRAW 4.2.

EXAMPLES

Without desiring to be limited thereto, the present invention will in the following be illustrated by way of examples.

Example 1: Synthesis of HA-BOR

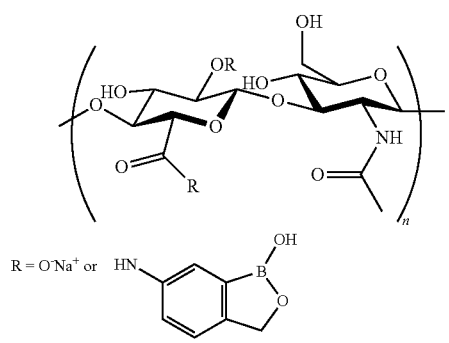

The amine-acid coupling agent 4-(4,6-dimethoxy-1,3,5-triazin-2-yl)-4-methylmorpholinium chloride (DMTMM) was dissolved in 1 mL of water and was added to a solution of native HA in a mixture of water/DMF (3/2, v/v). A concentration of HA in the reaction medium of 3 g/L was used for HA samples of 75 and 100 kg/mol, whereas 2 g/L was used for HA with 600 kg/mol. Then, 5-amino-2-hydroxymethylphenylboronic acid hydrochloride (1-hydroxy-3H-2,1-benzoxaborol-amine, ABOR) solubilized in 1 mL of water was added to the reaction medium. The pH was adjusted to 6.5 using 0.5 M HCl or NaOH and the reaction was kept under stirring at room temperature for 24 h. The product was purified by diafiltration with ultrapure water and was recovered by freeze-drying. The degree of substitution (DS) of HA-BOR was determined by $^1$H NMR ($DS_{NMR}$), and were also estimated from the reaction kinetics performed using 2,4,6-Trinitrobenzene Sulfonic Acid ($DS_{TNBS}$). This method consisted in quantifying the free primary amines in the reaction medium as a function of time. Table 1 summarizes the DMTMM/HA and BOR/HA molar ratios used for the syntheses with different $M_w$ HA, as well as the DS and the yields of HA-BOR conjugates.

HA-BOR: $^1$H NMR (400 MHz, D$_2$O) $\delta_H$ (ppm) 4.55 (H-1 from N-acetylglucosamine unit), 4.25 (H-1 from glucuronic acid), 3.9-3.1 (H-2, H-3, H-4, H-5, H-6 protons of HA), 2.08 (CH$_3$—CO from HA), 7.95 (s, 1H, NH—C—CH—C—B from Ph), 7.72 (m, 1H, C—CH—CH—C—C—B from Ph), 7.55 (m, 1H, C—CH—CH—C—C—B from Ph), 5.13 (s, 2H, CH$_3$—O—B).

Example 2: Synthesis of HA-PBA (Comparative Example)

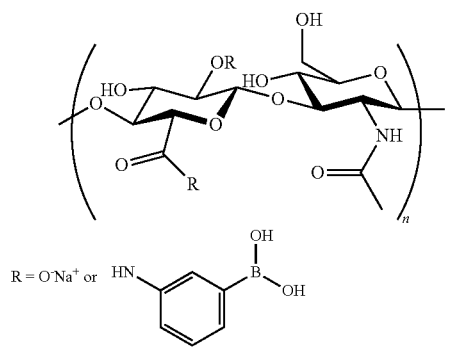

Grafting of phenylboronic acid was done according to Example 1, but using 3-aminophenylboronic acid hemisulfate salt (APBA) instead of 5-amino-2-hydroxymethylphenylboronic acid hydrochloride (ABOR). The degree of substitution (DS) of HA-PBA was determined by $^1$H NMR ($DS_{NMR}$), and were also estimated from the reaction kinetics performed using 2,4,6-Trinitrobenzene Sulfonic Acid ($DS_{TNBS}$). This method consisted in quantifying the free primary amines in the reaction medium as a function of time. Table 1 summarizes the DMTMM/HA and PBA/HA molar ratios used for the syntheses with different $M_w$ HA, as well as the DS and the yields of HA-PBA conjugates.

HA-PBA: $^1$H NMR (400 MHz, D$_2$O) $\delta_H$ (ppm) 4.55 (H-1 from N-acetylglucosamine unit), 4.25 (H-1 from glucuronic acid), 3.9-3.1 (H-2, H-3, H-4, H-5, H-6 protons of HA), 2.08 (CH$_3$—CO from HA), 7.93 (s, 1H, NH—C—CH—C—B from Ph), 7.7 (m, 2H, C—CH—CH—CH—C—B from Ph), 7.55 (m, 1H, C—CH—CH—CH—C—B from Ph).

TABLE 1

Syntheses of HA-BOR and HA-PBA.

| HA-boronic acid derivative | $M_w$ HA (Kg/mol) | DMTMM/HA molar ratio | BOR or PBA/HA molar ratio | $DS_{NMR}^a$ | $DS_{TNBS}$ | Yield (%)$^b$ |
|---|---|---|---|---|---|---|
| HA-BOR | 75 | 1 | 0.16 | 0.16 | 0.16 | 75 |
| HA-BOR | 100 | 1 | 0.16 | 0.12 | 0.14 | 85 |
| HA-BOR | 600 | 1 | 0.14 | 0.11 | 0.13 | 75 |
| HA-PBA | 75 | 1 | 0.16 | 0.16 | 0.16 | 75 |
| HA-PBA | 100 | 1 | 0.16 | 0.16 | 0.16 | 77 |
| HA-PBA | 600 | 1 | 0.14 | 0.14 | 0.14 | 78 |

$^a$DS by $^1$H NMR: 10% of accuracy.
$^b$HA-BOR or HA-PBA yield: calculation considering the $DS_{NMR}$.

Example 3: Synthesis of Pentenoate-Modified HA

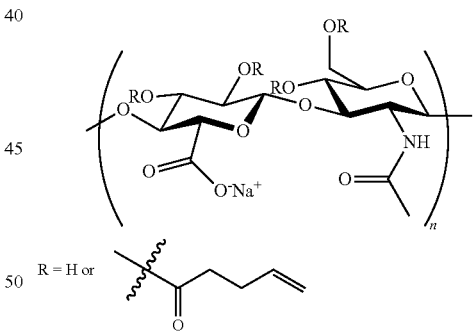

HA (1 g, 2.5 mmol, $M_w$=100 kg/mol) was dissolved in ultrapure water (50 mL) under continuous stirring overnight at 4° C. DMF (33 mL) was then added dropwise in order to have a water/DMF ratio of (3/2, v/v). 4-pentenoic anhydride (0.454 g, 2.5 mmol) was added while maintaining the pH between 8 and 9 by adding 1 M NaOH for at least 4 h. The reaction was kept at 4° C. under stirring for one night. The product was purified by diafiltration with ultrapure water and was recovered by freeze-drying. The degree of substitution (DS) of HA-pentenoate was found to be 0.18±0.01 by $^1$H NMR. A yield of 49% was calculated considering its DS.

$^1$H NMR (400 MHz, D$_2$O) $\delta_H$ (ppm) 4.71 (H-1 from N-acetylglucosamine unit), 4.53 (H-1 from glucuronic acid), 4.13-3.2 (H-2, H-3, H-4, H-5, H-6 protons of HA), 2.1

(CH₃—CO from HA), 6.0 (m, 1H, CH=CH₂), 5.18 (m, 2H, CH=CH₂), 2.62 (m, 2H, CH₃—C=O), 2.45 (m, 2H, OCCH₂—CH₂).

Example 4: Synthesis of HA-Maltose

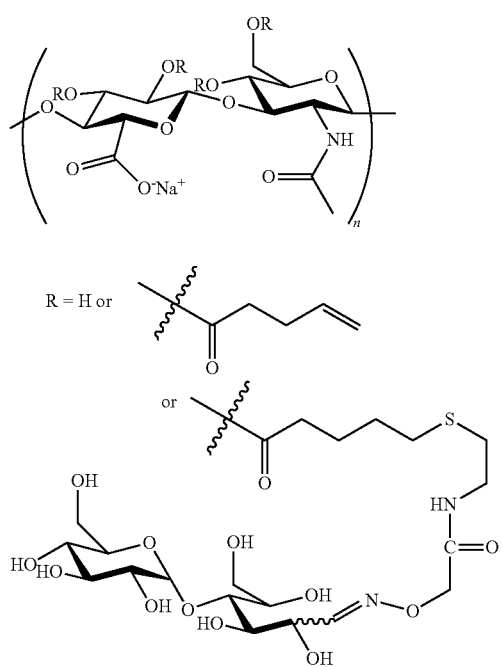

a. Maltose-Disulfide

To an aqueous solution of maltose (0.25 g, 0.694 mmol) in 25 mL of ultrapure water at room temperature, O-(carboxymethyl)hydroxylamine hemihydrochloride (0.0768 g, 0.694 mmol) was added. The pH was adjusted to 4.8 using 0.5 M NaOH. The reaction mixture was stirred for 24 hours at room temperature and then, was neutralized to pH 7 by addition of 0.5 M NaOH. The maltose-COOH derivative was then recovered by freeze-drying without further purification as a white powder (46 mol % of maltose-COOH/maltose). To a solution of maltose-COOH (0.25 g, 0.622 mmol) in dry DMF (50 mL), hydroxybenzotriazole (HOBt) (0.1875 g, 1.39 mmol), diisopropylcarbodiimide (DIC) (0.3483 g, 2.8 mmol) and cystamine dihydrochloride (0.094 g, 0.42 mmol) were successively added. The resulting mixture was stirred overnight at room temperature under nitrogen. After evaporation of most of the solvent, the residual syrup was poured dropwise into acetone (500 mL) under stirring. The white precipitate was collected by filtration, washed three times with acetone and dried to give the desired maltose-disulfide in 60% yield (0.295 g, 0.625 mmol).

$^1$H NMR (400 MHz, D₂O) $\delta_H$ (ppm) 7.75 (1H, anomeric H$_\beta$ from linked glucose unit, N=CH$_\beta$—), 7.13 (1H, anomeric Hα from linked glucose unit, N=CH$_\alpha$—), 5.4 (1H, anomeric H from pendant glucose unit of maltose), 5.19 (1H, anomeric Hα from linked glucose unit), 5.14 (1H, anomeric H from pendant glucose unit of maltose-disulfide), 4.7 (1H, anomeric H$_\beta$ from pendant glucose unit), 4.66 (2H, N—O—CH₂), 4.6 (1H, N=CH$_{\alpha,\beta}$—CH(OH) from linked glucose group), 3.4-4.2 (8H, H-3, H-4, H-5, H-6 from linked and pendant glucose groups), 2.95 (4H, NH—CH₂—CH₂).

b. HA-Maltose

The first step consisted in reducing the disulfide bond of maltose-disulfide. Thus, to an aqueous solution of this derivative (0.2 g, 0.211 mmol) in 4 mL of degassed phosphate buffered saline (PBS) pH 7.4 at room temperature, a solution of TCEP (91 mg, 0.317 mmol) in 1 mL of degassed PBS was added and the pH was adjusted to 5-5.5. The mixture was stirred for 15 min under nitrogen at room temperature to give maltose-SH. The pH was adjusted to 7.4 using 0.5 M NaOH and the mixture was added to HA-pentenoate solubilized in PBS in the presence of Irgacure 2959 (0.1%, w/v) as a photoinitiator. The grafting of maltose-SH moieties was performed under UV radiation (λ=365 nm, at 20 mW/cm² for 15 min). The product was purified by diafiltration with ultrapure water and was recovered by freeze-drying. The degree of substitution (DS) of HA-maltose was found to be 0.1±0.01 by $^1$H NMR.

$^1$H NMR (400 MHz, D₂O) $\delta_H$ (ppm) 4.55 (H-1 from N-acetylglucosamine unit), 4.25 (H-1 from glucuronic acid), 3.9-3.1 (H-2, H-3, H-4, H-5, H-6 protons of HA), 1.85 (CH₃—CO from HA), 1.52 (m, 2H, CH2-CH2-CH2-S), 1.62 (m, 2H, CH2-CH2-CH2-S), 2.35 (m, 2H, OC—CH₂) 2.63 (m, 2H, CH2-CH2-CH2-S), 2.82 (m, 2H, S—CH₂—CH₂—NH), 7.63 (m, 1H, H anomer of maltose).

Example 5: Synthesis of HA-Lactobionic

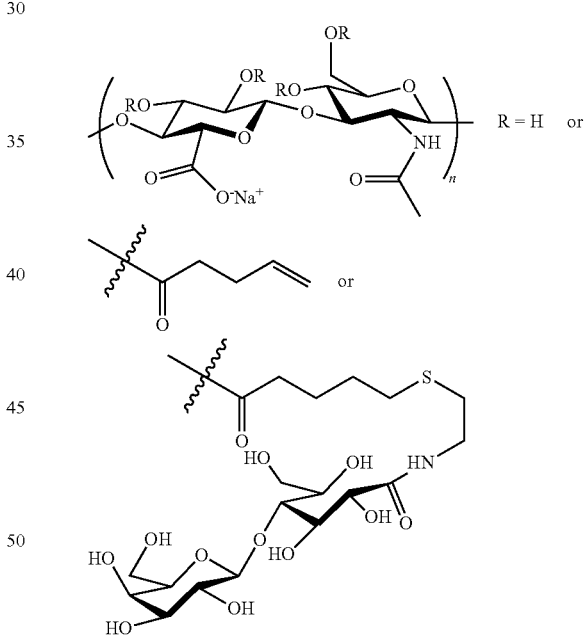

a. Lactobionic-Disulfide

To a solution of lactobionic acid (0.5023 g, 1.39 mmol) in dry DMF (50 mL), hydroxybenzotriazole (HOBt) (0.3768 g, 2.79 mmol), diisopropylcarbodiimide (DIC) (0.705 g, 5.56 mmol) and cystamine dihydrochloride (0.141 g, 0.626 mmol) were successively added. The resulting mixture was stirred overnight at room temperature under nitrogen. After evaporation of most of the solvent, the residual syrup was poured dropwise into acetone (500 mL) under stirring. The white precipitate was collected by filtration, washed three times with acetone and dried to give the desired lactobionic-disulfide in 29% yield (0.2362 g, 0.585 mmol).

b. HA-Lactobionic

A first step of reduction of the disulfide bond of the lactobionic-disulfide derivative (0.2 g, 0.211 mmol) dissolved in 1 mL of degassed PBS was performed by adding TCEP (91 mg, 0.317 mmol) in 1 mL of degassed PBS, with pH adjusted to 5-5.5. The mixture was stirred for 15 min under nitrogen at room temperature to give lactobionic-SH. The pH was adjusted to 7.4 using 0.5 M NaOH and the mixture was added to HA-pentenoate solubilized in PBS in the presence of Irgacure 2959 (0.1%, w/v) as a photoinitiator. The grafting of lactobionic-SH moieties was performed under UV radiation ($\lambda$=365 nm, at 20 mW/cm² for 15 min). The product was purified by diafiltration with ultrapure water and was recovered by freeze-drying. The degree of substitution (DS) of HA-lactobionic was found to be 0.2±0.01 by ¹H NMR.

Example 6: Synthesis of HA-Fructose

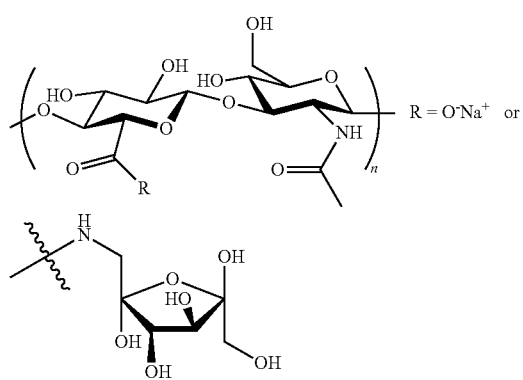

1-amino-1-deoxy-D-fructose hydrochloride (0.0121 g, 0.056 mmol) dissolved in 1 mL of ultrapure water was added to a solution of native HA (0.15 g, 0.374 mmol) in a mixture of water/DMF (3/2, v/v) in the presence of 4-(4,6-dimethoxy-1,3,5-triazin-2-yl)-4-methylmorpholinium chloride (DMTMM) (0.1035 g, 0.374 mmol) as an amine-acid coupling agent. The pH was adjusted to 6.5 using 0.5 M HCl or NaOH and the reaction was kept under stirring at room temperature for 24 h. The product was purified by diafiltration with ultrapure water and was recovered by freeze-drying. The degree of substitution (DS) of HA-fructose was determined by ¹³C NMR ($DS_{NMR}$=0.15±0.01), and was also estimated from the reaction kinetics performed using 2,4,6-Trinitrobenzene Sulfonic Acid ($DS_{TNBS}$=0.14). A yield of 84% was determined for HA-fructose (considering its $DS_{NMR}$).

¹H NMR (400 MHz, D₂O) $\delta_H$ (ppm) 4.62 (H-1 from N-acetylglucosamine unit), 4.46 (H-1 from glucuronic acid), 4.05-3.2 (18H, H-2, H-3, H-4, H-5, H-6 protons of HA and of fructose moieties), 2.02 (CH₃—CO from HA).

Example 7: Synthesis of HA-Sorbitol

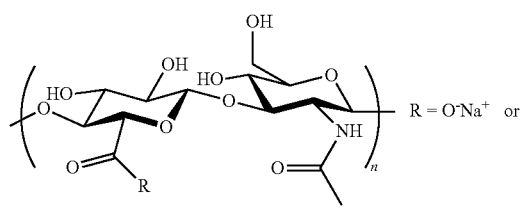

-continued

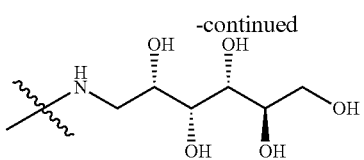

1-amino-1-deoxy-D-sorbitol hydrochloride (D-glucamine) (0.0088 g, 0.05 mmol) dissolved in 1 mL of ultrapure water was added to a solution of native HA (0.1305 g, 0.325 mmol) in ultrapure water in the presence of 4-(4,6-dimethoxy-1,3,5-triazin-2-yl)-4-methylmorpholinium chloride (DMTMM) (0.09 g, 0.325 mmol) as an amine-acid coupling agent. The pH was adjusted to 6.5 using 0.5 M HCl or NaOH and the reaction was kept under stirring at room temperature for 164 h. The product was purified by diafiltration with ultrapure water and was recovered by freeze-drying. The degree of substitution (DS) of HA-sorbitol was determined by ¹³C NMR ($DS_{NMR}$=0.15±0.1), and was also estimated from the reaction kinetics performed using 2,4,6-Trinitrobenzene Sulfonic Acid ($DS_{TNBS}$=0.1). A yield of 76% was determined for HA-sorbitol (considering its $DS_{NMR}$).

¹H NMR (400 MHz, D₂O) $\delta_H$ (ppm) 4.68 (H-1 from N-acetylglucosamine unit), 4.51 (H-1 from glucuronic acid), 4.1-3.3 (19H, H-2, H-3, H-4, H-5, H-6 protons of HA and of sorbitol moieties), 2.07 (CH₃—CO from HA).

Example 8: Preparation of HA-BOR/HA-polyol Gel

Solutions of HA-BOR and of the HA-polyol derivatives (HA-maltose or HA-lactobionic or HA-fructose or HA-sorbitol) were prepared at 15 g/L in 0.01 M HEPES buffer containing 0.15 M NaCl pH 7.4, and were kept under stirring overnight at 4° C. Combinations of HA-BOR/HA-polyol derivative, were prepared by mixing a solution containing HA-BOR with a solution containing a HA-polyol derivative at physiological pH, at a total polymer concentration of 15 g/L and with BOR/polyol molar ratio of 1/1.

Results: When gels were formed quasi-instantaneously upon mixing HA-BOR solution with a solution of a HA-polyol derivative. Characteristics of the resulting HA-BOR/HA-polyol mixtures are summarized in Table 2.

Example 9: Preparation of HA-PBA/HA-Polyol Gel (Comparative Example)

HA-PBA/HA-polyol gels were prepared according to example 8, but using HA-PBA instead of HA-BOR.

Results: When gels were formed quasi-instantaneously upon mixing HA-BOR solution with a solution of a HA-polyol derivative. Characteristics of the resulting HA-PBA/HA-polyol mixtures are summarized in Table 2.

TABLE 2

Characteristics of HA-BOR/HA-polyol and HA-PBA/HA-polyol
mixtures in 0.01M HEPES buffer containing 0.15M NaCl pH 7.4
([PS] = 15 g/L, BOR or PBA/fructose molar ratio = 1/1).

| HA-boronic acid | DS HA-boronic acid | HA-polyol | DS HA-polyol | $M_w$ HA (kg/mol) | G' 1 Hz (Pa) | G" 1 Hz (Pa) | Rheological behavior |
|---|---|---|---|---|---|---|---|
| HA-BOR | 0.15 | HA-maltose | 0.12 | 75 | 34 | 20 | Viscoelastic |
| HA-BOR | 0.15 | HA-fructose | 0.15 | 75 | 515 | 17 | Gel |
| HA-BOR | 0.15 | HA-sorbitol | 0.15 | 75 | 250 | 125 | Viscoelastic |
| HA-BOR | 0.1 | HA-fructose | 0.15 | 100 | 280 | 30 | Gel |
| HA-BOR | 0.15 | HA-fructose | 0.15 | 100 | 275 ± 35 | 20.5 ± 2.5 | Gel |
| HA-BOR | 0.12 | HA-lactobionic | 0.2 | 100 | 87 | 33 | Viscoelastic |
| HA-BOR | 0.1 | HA-fructose | 0.08 | 600 | 250 | 80 | Gel |
| HA-PBA | 0.15 | HA-maltose | 0.12 | 75 | 490 | 7 | Gel |
| HA-PBA | 0.15 | HA-fructose | 0.15 | 75 | 447 | 6.6 | Gel |
| HA-PBA | 0.15 | HA-sorbitol | 0.15 | 75 | 150 | 45 | Viscoelastic |
| HA-PBA | 0.15 | HA-fructose | 0.15 | 100 | 227 ± 12 | 8 ± 1.5 | Gel |
| HA-PBA | 0.15 | HA-lactobionic | 0.2 | 100 | 439 | 21 | Gel |
| HA-PBA | 0.15 | HA-fructose | 0.08 | 600 | 91 | 27 | Gel |

Example 10: The Effect of a Higher Degree of Substitution (DS) on the Behavior of HA-BOR/HA-Fructose and HA-PBA/HA-Fructose Gels HA-BOR/HA-fructose and HA-PBA/fructose gels were prepared according to example 8, but using HA-BOR and HA-PBA derivatives with higher DS of 0.4 and 0.5, respectively.

Results: Gels were formed quasi-instantaneously upon mixing HA-BOR solution with a solution of a HA-fructose. Characteristics of the resulting HA-BOR or HA-PBA/HA-fructose mixtures are summarized in Table 3. Higher dynamic moduli (G' and G") were obtained for the HA-BOR/HA-fructose hydrogel when using HA-BOR with a higher DS, compared to the mixture using HA-PBA with a DS of 0.5 (FIG. 1). Viscosity measurements showed that cross-links formed between BOR moieties and HA hydroxyl groups lead to increase the viscosity of HA network (FIG. 1). Therefore, the double crosslinking of BOR/fructose moieties and BOR/HA contribute to improve gel properties, in opposition to the HA-PBA/HA-fructose mixture.

Example 11: HA-Benzoboroxole (HA-BOR)/HA-Polyol

Figure 2:
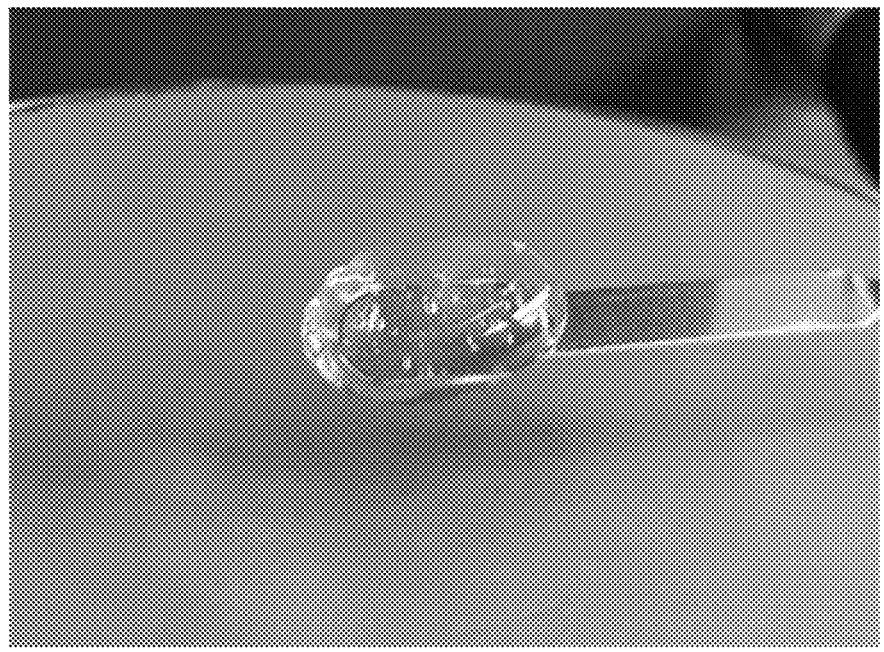
FIG. 2: Photo of a gel obtained with HA-BOR/HA-polyol

Gels obtained from mixtures of benzoboroxole modified HA (HA-BOR)/HA-polyol were prepared by simply mixing solutions of the two HA partners solubilized in 0.01 M HEPES buffer with 0.15 M NaCl at physiological pH. When these solutions were mixed at a total polymer concentration of 15 g/L, and with benzoboroxole/polyol molar ratio of 1/1, transparent gels were formed quasi-instantaneously (FIG. 2).

Figure 3:
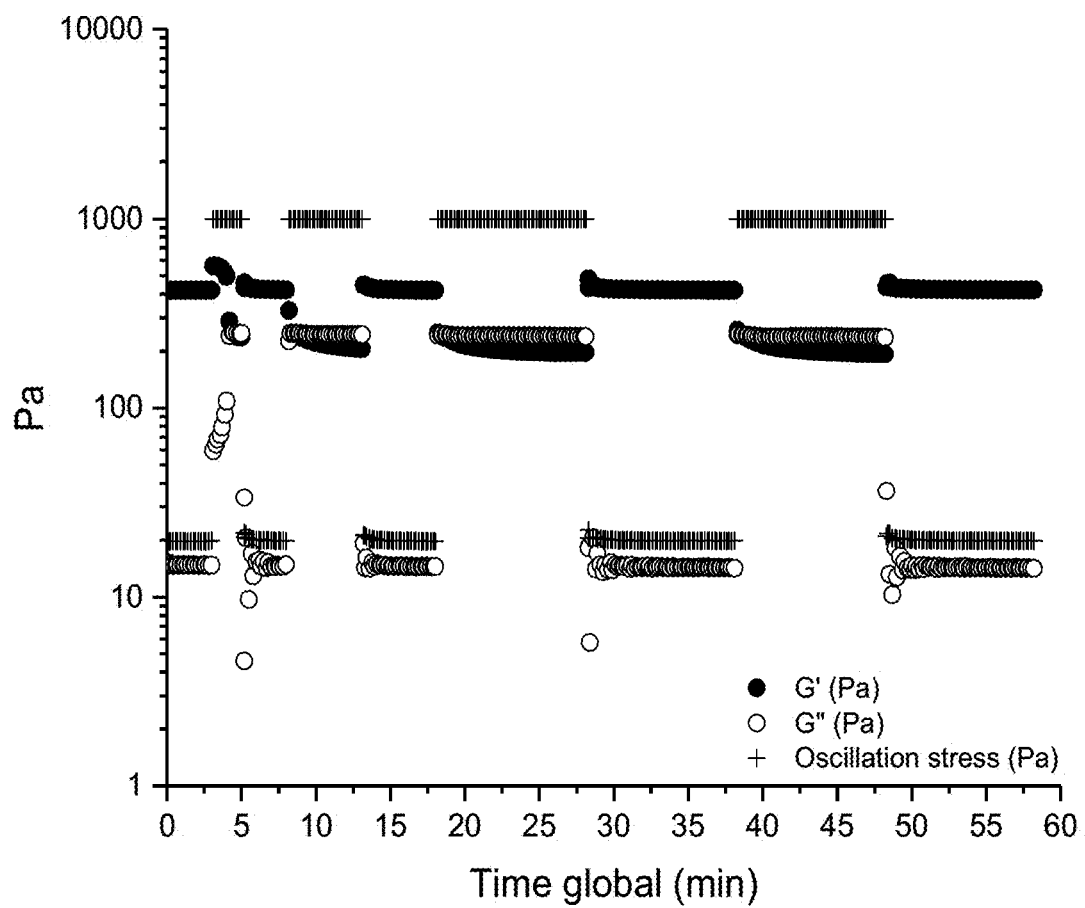
FIG. 3: Self-healing properties of a dynamic gel of HA-BOR/HA-fructose (CHA=15 g/L) at 25° C.: stress recovery of the hydrogel after four cycles of recovery from stress-induced breakdowns at pH 7.4.

Results: Characteristics of the resulting HA-BOR/HA-polyol mixtures are summarized in Table 4. Self-healing properties of a dynamic gel of HA-BOR/HA-fructose (CHA=15 g/L) at 25° C. were investigated by, while measuring G' and G", applying successive stress values from 1800 to 2100 Pa for 2 min. These were intercalated with short time periods in which low stress values (corresponding to 5% strain) were applied for 3 min. This experiment demonstrated the stress recovery of the HA-BOR/HA-fructose gel after 4 cycles of stress-induced breakdowns. Large stress (from 1800 to 2100 Pa) inverted the values of G' (filled circles) and G" (empty circles), indicating breakage of crosslinks and conversion to solution state. G' was recovered under a small strain (5%) within few seconds. These gels provide self-healing properties (FIG. 3).

TABLE 3

Characteristics of HA-BOR/HA-polyol and HA-PBA/HA-polyol
mixtures in 0.01M HEPES buffer containing 0.15M NaCl pH 7.4
([PS] = 15 g/L, BOR or PBA/fructose molar ratio = 1/1).

| HA-boronic acid | DS HA-boronic acid | HA-polyol | DS HA-polyol | Mw HA (kg/mol) | G' 1 Hz (Pa) | G" 1 Hz (Pa) | Rheological behavior |
|---|---|---|---|---|---|---|---|
| HA-BOR | 0.4 | HA-fructose | 0.15 | 100 | 350 | 17 | Gel |
| HA-PBA | 0.5 | HA-fructose | 0.15 | 100 | 185 | 5 | Gel |

TABLE 4

Characteristics of HA-BOR/HA-Polyol hydrogel

| DS HA-BOR derivative | HA-polyol derivative | DS HA-polyol derivative | Mw HA (kg/mol) | G' 1 Hz (Pa) | G" 1 Hz (Pa) | Rheological behavior |
|---|---|---|---|---|---|---|
| 0.16 | HA-maltose | 0.12 | 75 | 34 | 20 | Viscoelastic |
| 0.16 | HA-fructose | 0.15 | 75 | 500 | 17 | Gel |
| 0.16 | HA-sorbitol | 0.15 | 75 | 250 | 125 | Viscoelastic |
| 0.12 | HA-fructose | 0.15 | 100 | 490 | 7 | Gel |
| 0.11 | HA-fructose | 0.08 | 600 | 250 | 80 | Gel |

Example 12: Synthesis of HA-1-hydroxy-7-methoxy-3H-2,1-benzoxaborol-6-amine

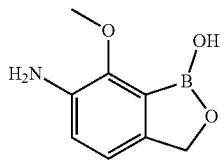

Example 12 is performed according to Example 1, but using 1-hydroxy-7-methoxy-3H-2,1-benzoxaborol-6-amine hydrochloride as the ABOR derivative instead of 1-hydroxy-3H-2,1-benzoxaborol-amine hydrochloride.

Example 13: HA-1-hydroxy-7-methoxy-3H-2,1-benzoxaborol-6-amine/HA-polyol Gel Preparation Gels are prepared according to example 8, but using HA-1-hydroxy-7-methoxy-3H-2,1-benzoxaborol-6-amine instead of HA-BOR.

Example 14: Synthesis of HA-7-fluoro-1-hydroxy-3H-2,1-benzoxaborol-6-amine

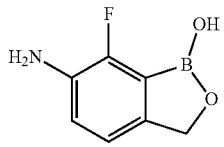 [SMILES: Nc1ccc2c(c1F)B(O)OC2]

Example 14 is performed according to Example 1, but using 7-fluoro-1-hydroxy-3H-2,1-benzoxaborol-6-amine hydrochloride as the ABOR derivative instead of 1-hydroxy-3H-2,1-benzoxaborol-amine hydrochloride.

Example 15: HA-7-fluoro-1-hydroxy-3H-2,1-benzoxaborol-6-amine/HA-polyol Gel Preparation Gels are prepared according to example 8, but using HA-7-fluoro-1-hydroxy-3H-2,1-benzoxaborol-6-amine instead of HA-BOR.

Example 16: Synthesis of HA-(1-hydroxy-3H-2,1-benzoxaborol-6-yl)methanamine

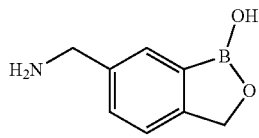 [SMILES: NCc1ccc2c(c1)B(O)OC2]

Example 16 is performed according to Example 1, but using (1-hydroxy-3H-2,1-benzoxaborol-6-yl)methanamine hydrochloride as the ABOR derivative instead of 1-hydroxy-3H-2,1-benzoxaborol-amine hydrochloride.

Example 17: HA-(1-hydroxy-3H-2,1-benzoxaborol-6-yl)methanamine/HA-polyol Gel Preparation Gels are prepared according to example 8, but using HA-(1-hydroxy-3H-2,1-benzoxaborol-6-yl)methanamine instead of HA-BOR.

Example 18: Synthesis of HA-1-hydroxy-3,3-dimethyl-2,1-benzoxaborol-6-amine

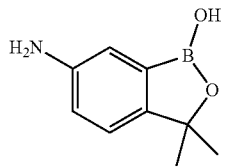

Example 18 is performed according to Example 1, but using 1-hydroxy-3,3-dimethyl-2,1-benzoxaborol-6-amine hydrochloride as the ABOR derivative instead of 1-hydroxy-3H-2,1-benzoxaborol-amine hydrochloride.

Example 19: HA-1-hydroxy-3,3-dimethyl-2,1-benzoxaborol-6-amine/HA-polyol Gel Preparation Gels are prepared according to example 8, but using HA-1-hydroxy-3,3-dimethyl-2,1-benzoxaborol-6-amine instead of HA-BOR.

Example 20: Synthesis of HA-1-hydroxy-3,4-dihydro-2,1-benzoxaborinin-7-amine

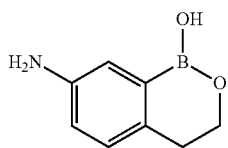 [SMILES: Nc1ccc2c(c1)B(O)OCC2]

Example 20 is performed according to Example 1, but using 1-hydroxy-3,4-dihydro-2,1-benzoxaborinin-7-amine hydrochloride as the ABOR derivative instead of 1-hydroxy-3H-2,1-benzoxaborol-amine hydrochloride.

Example 21: HA-1-hydroxy-3,4-dihydro-2,1-benzoxaborinin-7-amine/HA-polyol Gel Preparation Gels are prepared according to example 8, but using HA-1-hydroxy-3,4-dihydro-2,1-benzoxaborinin-7-amine instead of HA-BOR.

Example 22: Synthesis of HA-(1-hydroxy-3H-2,1-benzoxaborol-6-yl)methanamine

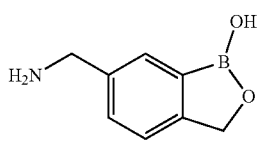 [SMILES: NCc1ccc2c(c1)B(O)OC2]

Example 22 was performed according to Example 1, but using (1-hydroxy-3H-2,1-benzoxaborol-6-yl)methanamine hydrochloride (AMBOR) as the ABOR derivative instead of 1-hydroxy-3H-2,1-benzoxaborol-amine hydrochloride. The molecular weight of the Hyaluronic acid was 100 kg/mol.

Example 23: HA-(1-hydroxy-3H-2,1-benzoxaborol-6-yl)methanamine/HA-polyol Gel Preparation Gels were prepared according to example 8, but using HA-(1-hydroxy-3H-2,1-benzoxaborol-6-yl)methanamine (HA-AMBOR) instead of HA-BOR.

Example 24: Synthesis of HA-1-hydroxy-3,3-dimethyl-2,1-benzoxaborol-6-amine

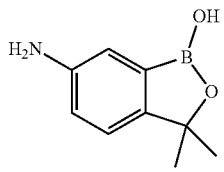

Example 24 was performed according to Example 1, but using 1-hydroxy-3,3-dimethyl-2,1-benzoxaborol-6-amine hydrochloride (DMABOR) as the ABOR derivative instead of 1-hydroxy-3H-2,1-benzoxaborol-amine hydrochloride. The molecular weight of the Hyaluronic acid was 100 kg/mol.

Example 25: HA-1-hydroxy-3,3-dimethyl-2,1-benzoxaborol-6-amine/HA-polyol Gel Preparation Gels were prepared according to example 8, but using HA-1-hydroxy-3,3-dimethyl-2,1-benzoxaborol-6-amine (HA-100DMABOR) instead of HA-BOR.

Example 26: Synthesis of HA-7-fluoro-1-hydroxy-3H-2,1-benzoxaborol-6-amine

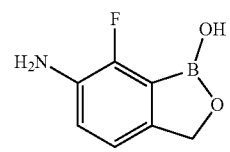 [SMILES: Nc1ccc2c(c1F)B(O)OC2]

Example 26 was performed according to Example 1, but using 7-fluoro-1-hydroxy-3H-2,1-benzoxaborol-6-amine hydrochloride (FBOR) as the ABOR derivative instead of 1-hydroxy-3H-2,1-benzoxaborol-amine hydrochloride. The molecular weight of the Hyaluronic acid was 100 kg/mol.

Example 27: HA-1-hydroxy-3,3-dimethyl-2,1-benzoxaborol-6-amine/HA-polyol Gel Preparation Gels were prepared according to example 8, but using 7-fluoro-1-hydroxy-3H-2,1-benzoxaborol-6-amine (HA-FBOR) instead of HA-BOR.

Example 28: Rheological Behavior of Gels Using HA-BOR Derivatives, Compared to HA-PBA

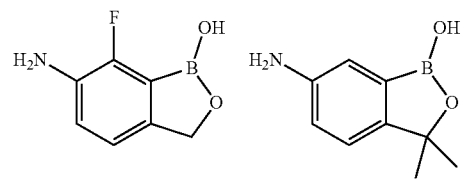

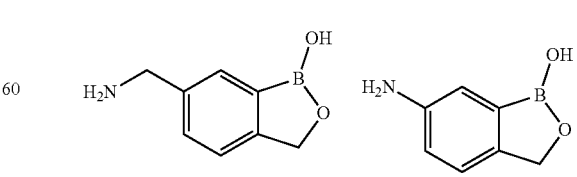

Results: Characteristics of the resulting HA-BOR/HA-polyol mixtures are summarized in Table 5.

TABLE 5

HA100-boronic acid/HA100-fructose mixtures analyzed by rheology
([PS] = 15 q/L; BOR or DMABOR or AMBOR or FBOR or PBA/fructose molar
ratio = 1; 0.01M HEPES/0.15M NaCl buffer pH 7.4).

| HA-boronic acid | DS of HA-boronic acid | DS of HA-fructose | Rheological behavior | G' 1 Hz (Pa) | G" 1 Hz (Pa) |
|---|---|---|---|---|---|
| HA100-BOR | 0.15 | 0.15 | Gel | 275 ± 35 | 20.5 ± 2.5 |
| HA100-FBOR | 0.12 | 0.15 | Gel | 525 ± 11 | 14 ± 2.8 |
| HA100-DMABOR | 0.14 | 0.15 | Gel | 120 ± 32 | 7 ± 1.3 |
| HA100-AMBOR | 0.12 | 0.15 | Gel/Viscoelastic | 116 ± 9 | 12 ± 1.3 |
| HA100-PBA | 0.16 | 0.15 | Gel | 227 ± 12 | 8 ± 1.5 |

Figure 4A:
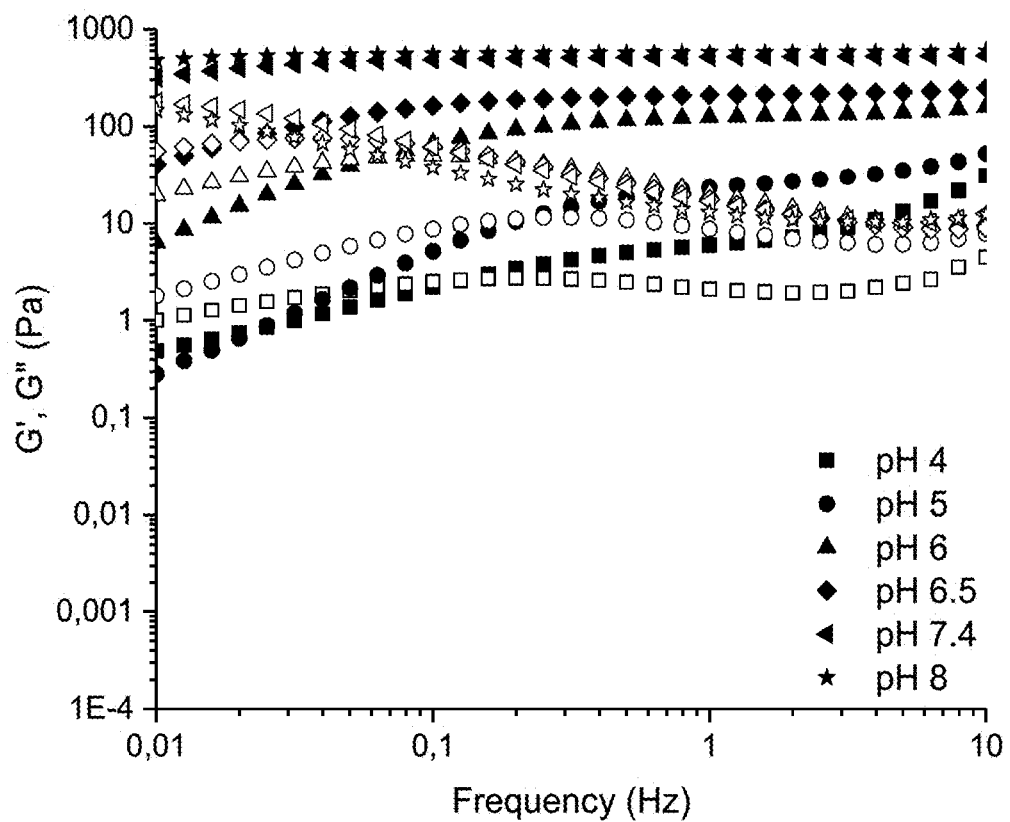
FIGS. 4A-4C: Rheological analyses of HA-BOR/HA-fructose (A), HA-FBOR/HA-fructose (B) and HA-PBA/HA-fructose (C) mixtures in 0.01M HEPES buffer containing 0.15M NaCl at different pH (from 4 to 8).
Figure 4B:
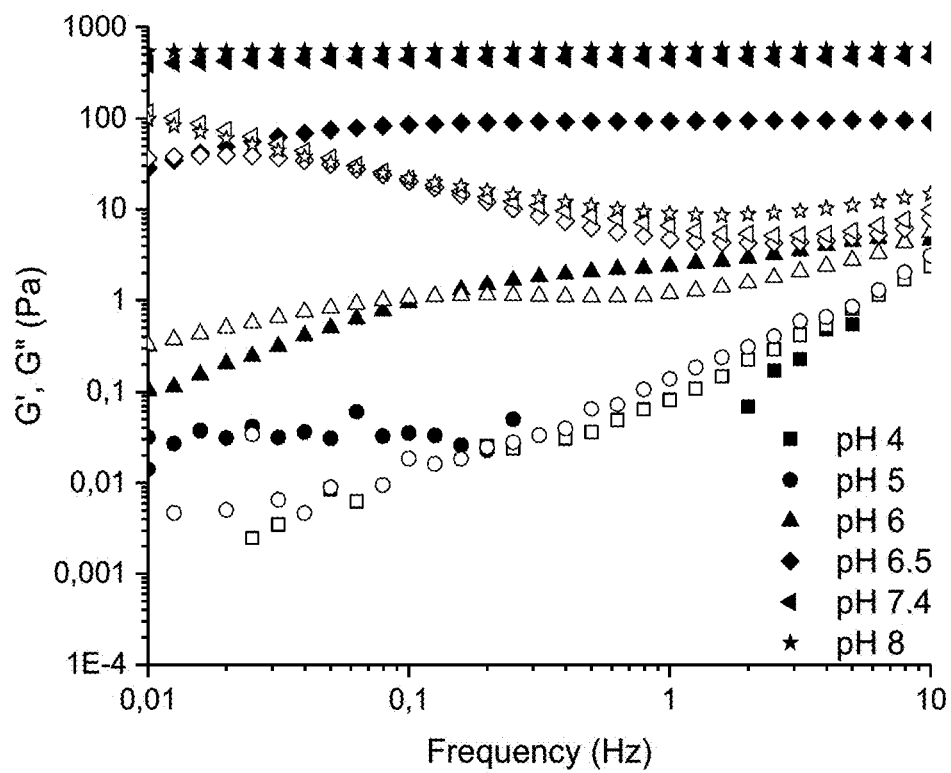
Figure 4C:
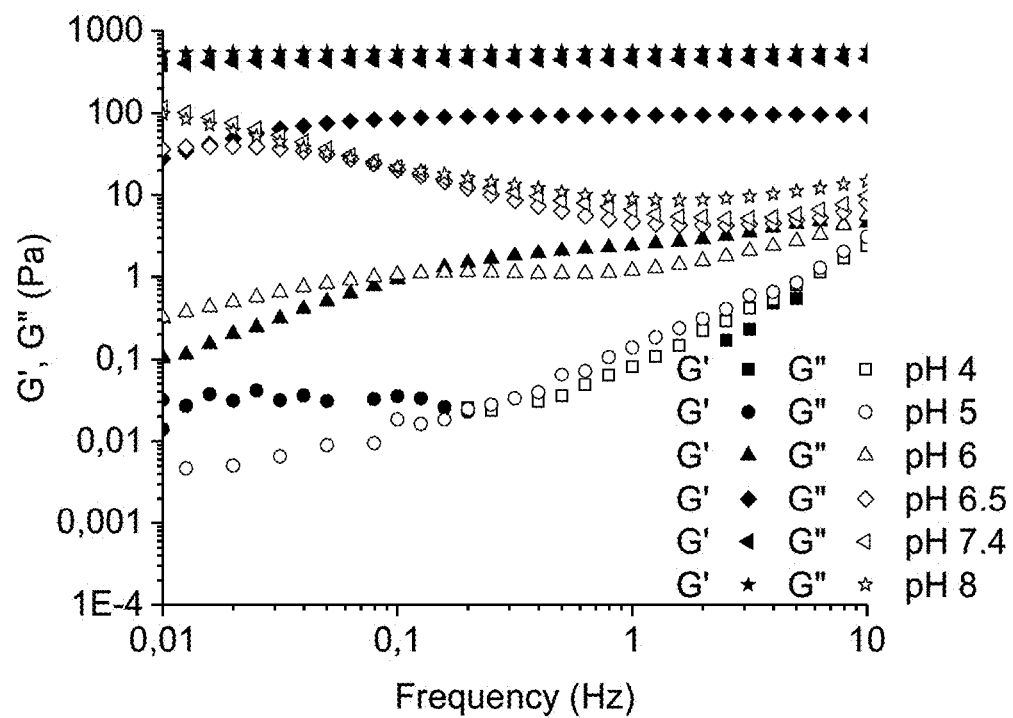

Example 29: The Effect of pH on the Behavior of HA-BOR/HA-Fructose or HA-FBOR/HA-Fructose and HA-PBA/HA-Fructose Gels Rheological analyses were performed to compare the effect of pH on the behavior of HA-BOR/HA-fructose or HA-FBOR/HA-fructose vs HA-PBA/HA-fructose gels (FIG. 4).

Results: Table 6 summarizes the characteristics of the gels at different pH. These results showed that a higher stability at a pH range from 4 to 8 was observed for the HA-BOR/HA-fructose and HA-FBOR/HA-fructose mixtures, compared to HA-PBA/HA-fructose (FIG. 4).

TABLE 6

Analyses of HA-BOR or HA-FBOR or HA-PBA/HA-fructose mixtures
in 0.01M HEPES buffer containing 0.15M NaCl at different pH ($M_w$ HA = 75 or
100 kq/mol, [PS] = 15 q/L, DS of HA-BOR or HA-PBA or HA-fructose = 0.15,
DS of HA-FBOR = 0.12, BOR or FBOR or PBA/fructose molar ratio = 1). Cross-
over frequency: <0.01 = near 0.01 Hz or <<0.01 = far below 0.01 Hz.

| HA-boronic acid derivative | pH | G' 1 Hz (Pa) | G" 1 Hz (Pa) | Cross-over frequency (Hz) |
|---|---|---|---|---|
| HA-BOR ($M_w$ = 75 kg/mol) | 4 | 6 | 2 | 0.13 |
| | 5 | 23.5 | 9 | 0.25 |
| | 6 | 125 | 20 | 0.063 |
| | 6.5 | 210 | 17.5 | 0.02 |
| | 7.4 | 515 | 17 | <0.01 |
| | 8 | 572 | 13 | <<0.01 |
| HA-FBOR ($M_w$ = 100 kg/mol) | 4 | 1.4 | 4 | G' < G" |
| | 5 | 19 | 22 | 1.3 |
| | 6 | 126 | 50 | 0.2 |
| | 6.5 | 332 | 50 | 0.025 |
| | 7.4 | 533 | 12 | <<0.01 |
| | 8 | 545 | 11 | <<0.01 |
| HA-PBA ($M_w$ = 75 kg/mol) | 4 | ≤0.1 | ≤0.1 | G' < G" |
| | 5 | ≤0.1 | ≤0.1 | G' < G" |
| | 6 | 2.4 | 1.2 | 0.13 |
| | 6.5 | 93.5 | 5 | 0.016 |
| | 7.4 | 447 | 7 | <<0.01 |
| | 8 | 564 | 9 | <<0.01 |

Example 30: Self Healing Properties of Obtained Gels

The variation of G' and G" as a function of time immediately after injection through a 27 gauge needle of HA-BOR/HA-fructose or HA-DMABOR/HA-fructose or HA-FBOR/HA-fructose gels was investigated. Gels were prepared in 0.01M HEPES/0.15M NaCl buffer pH 7.4, at a [PS]=15 g/L and BOR or DMABOR or FBOR/fructose molar ratios of 1/1).

Results:

The hydrogels exhibited self-healing properties. Consequently, they can be injected as preformed solids, because the solid gel can manage external damages and repair itself under a proper shear stress. Due to fast gelation kinetics after extrusion/injection, they recover their solid form immediately. As an example, FIG. 5 shows the variation of G' and G" as a function of time immediately after injection of HA-BOR/HA-fructose or HA-DMABOR/HA-fructose or HA-FBOR/HA-fructose gels through a 27 gauge needle. From this Figure, it can be seen that the three samples recovered into a solid gel quasi-instantaneously.

The invention claimed is:

1. Crosslinked hyaluronic acids, wherein said crosslinked hyaluronic acids are crosslinked via a phenylboronic acid crosslinker formed between a fructose moiety of a fructose modified hyaluronic acid of formula (HA-fructose):

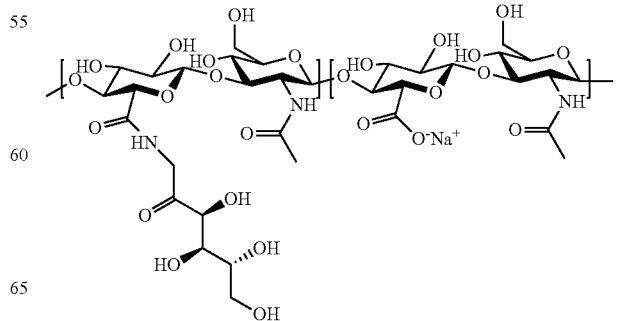

and a phenylboronic acid of a second hyaluronic acid grafted with the phenylboronic acid via an amide bond.

2. The crosslinked hyaluronic acids according to claim 1, wherein the second hyaluronic acid grafted with a phenylboronic acid has repetitive units of formula (HA-PBA):

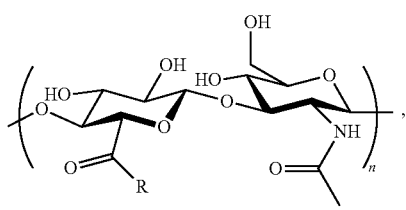

wherein in each unit, R is independently: provided that at least one R is:

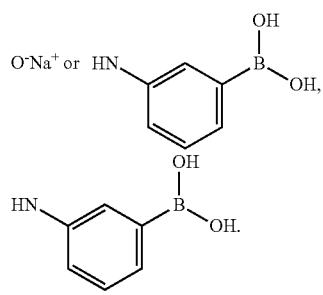

3. A polymer composition, comprising crosslinked hyaluronic acids according to claim 1 and an aqueous buffer.

4. The polymer composition comprising crosslinked hyaluronic acids according to claim 2 and an aqueous buffer.

* * * * *